(12) United States Patent
Hwang et al.

(10) Patent No.: US 8,053,768 B2
(45) Date of Patent: Nov. 8, 2011

(54) SILICON-CONTAINING COMPOUND AND ORGANIC ELECTROLUMINESCENT DEVICE EMPLOYING THE SAME

(75) Inventors: Seok-Hwan Hwang, Yongin (KR); Young-Kook Kim, Yongin (KR); Yoon-Hyun Kwak, Yongin (KR); Jeoung-In Yi, Yongin (KR); Jong-Hyuk Lee, Yongin (KR)

(73) Assignee: Samsung Mobile Display Co., Ltd., Nongseo-Dong, Giheung-Gu, Yongin, Gyunggi-Do (KR)

( * ) Notice: Subject to any disclaimer, the term of this patent is extended or adjusted under 35 U.S.C. 154(b) by 159 days.

(21) Appl. No.: 12/461,768

(22) Filed: Aug. 24, 2009

(65) Prior Publication Data

US 2010/0051914 A1     Mar. 4, 2010

(30) Foreign Application Priority Data

Sep. 3, 2008   (KR) .................. 10-2008-0086800

(51) Int. Cl.
*H01L 35/24* (2006.01)
*H01L 51/00* (2006.01)
(52) U.S. Cl. ............... 257/40; 257/E51.001; 428/1.23; 428/1.32; 428/1.52
(58) Field of Classification Search .............. 257/40, 257/E51.001; 428/1.23, 1.32, 1.52
See application file for complete search history.

(56) References Cited

FOREIGN PATENT DOCUMENTS

JP      2001-332385     11/2001

OTHER PUBLICATIONS

Korean Office action issued on Dec. 21, 2009, corresponding to Korean Priority Application No. 2008-0086800.
"Decreased Aggregation Phenomena in Polyfluorenes by Introducing Carbazole Copolymer Units." Macromolecules, 2001 (34) 5854-5859.

*Primary Examiner* — Kenneth Parker
*Assistant Examiner* — Anthony Ho
(74) *Attorney, Agent, or Firm* — Robert E. Bushnell, Esq.

(57) ABSTRACT

Provided are a silicon-containing compound having carbazole and fluorene in its molecule and an organic electroluminescent device including an organic layer employing the same. The silicon-containing compound is represented by the following formula:

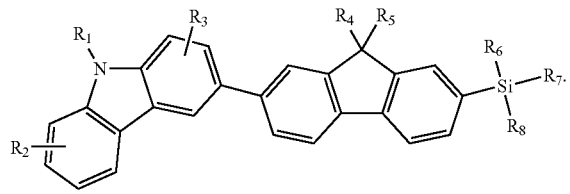

The silicon-containing compound has excellent electrical characteristics and a charge transporting capability, the silicon-containing compound can be used as a hole injecting material, a hole transporting material, and/or a light emitting material that are suitable for all-color fluorescent and phosphorescent organic light emitting devices such as red, green, blue, and white fluorescent and phosphorescent organic light emitting devices. When the silicon-containing compound is used to manufacture an organic electroluminescent device, the organic electroluminescent device has a high efficiency, a low driving voltage, high luminosity, and a long lifetime.

20 Claims, 2 Drawing Sheets

SILICON-CONTAINING COMPOUND AND ORGANIC ELECTROLUMINESCENT DEVICE EMPLOYING THE SAME

CROSS-REFERENCE TO RELATED PATENT APPLICATION AND CLAIM OF PRIORITY

This application claims the benefit of Korean Patent Application No. 10-2008-0086800, filed on Sep. 3, 2008, in the Korean Intellectual Property Office, the disclosure of which is incorporated herein in its entirety by reference.

BACKGROUND OF THE INVENTION

1. Field of the Invention

The present invention relates to a silicon-containing compound and an organic electroluminescent device employing the same.

2. Description of the Related Art

Electroluminescent devices are a self-emission type display device and have a wide viewing angle, a high contrast ratio, and a short response time. Due to such characteristics, electroluminescent devices are getting more attention.

Electroluminescent devices are generally classified into inorganic electroluminescent devices including an emitting layer employing an inorganic compound and organic electroluminescent devices including an emitting layer employing an organic compound. Specifically, organic electroluminescent devices have higher luminescent characteristics, a lower driving voltage, and a shorter response time than inorganic electroluminescent devices. In addition, organic electroluminescent devices produce various colors. Due to those characteristics, much research into organic electroluminescent devices is being performed. In general, an organic electroluminescent device has a stack structure of anode/organic emitting layer/cathode, or when a hole injection layer and/or a hole transport layer and/or an electron injection layer are further stacked between the anode and the emitting layer or between the emitting layer and the cathode, a stack structure of anode/hole transport layer/organic emitting layer/cathode or a stack structure of anode/hole transport layer/organic emitting layer/electron transport layer/cathode.

Meanwhile, a polyphenyl compound or anthracene derivatives are well known as a hole transport layer forming material (see U.S. Pat. No. 6,596,415 and U.S. Pat. No. 6,465,115). However, organic electroluminescent devices employing conventional hole injection layer and/or hole transport layer forming materials still needs to be improved in terms of lifetime, efficiency, and power consumption.

SUMMARY OF THE INVENTION

An embodiment of the present invention provides a silicon-containing compound for an organic electroluminescent device.

An embodiment of the present invention provides a silicon-containing compound having a high electrical stability, a high charge transporting capability, a high glass transition temperature, and a crystallization preventing capability, which is used as an organic layer forming material that is appropriate for use in all-color fluorescent and phosphorescent organic light emitting devices such as red, green, blue, and white fluorescent and phosphorescent organic light emitting devices.

An embodiment of the present invention also provides an improved organic electroluminescent device An embodiment of the present invention provides an organic electroluminescent device having high efficiency, a low driving voltage, and high luminosity and including an organic layer employing the silicon-containing compound, and a flat panel apparatus including the organic electroluminescent device.

According to an aspect of the present invention, there is provided a silicon-containing compound represented by Formula 1:

<Formula 1>

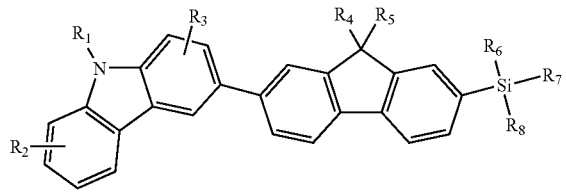

wherein $R_1$ is selected from a substituted or unsubstituted C1-C30 alkyl group, a substituted or unsubstituted C2-C30 alkenyl group, a substituted or unsubstituted C2-C30 alkynyl group, a substituted or unsubstituted C1-C30 alkoxy group, a substituted or unsubstituted C6-C30 aryloxy group, a substituted or unsubstituted C6-C30 aryl group, a substituted or unsubstituted C4-C20 heteroaryl group, and a substituted or unsubstituted C4-C30 condensed polycyclic group, $R_2$ and $R_3$ are, each independently, hydrogen, fluorine, a cyano, amino, a substituted or unsubstituted C1-C30 alkyl group, a substituted or unsubstituted C2-C30 alkenyl group, a substituted or unsubstituted C2-C20 alkynyl group, a substituted or unsubstituted C1-C30 alkoxy group, a substituted or unsubstituted C6-C30 aryloxy group, a substituted or unsubstituted C6-C20 aryl group, a substituted or unsubstituted C4-C20 heteroaryl group, or a substituted or unsubstituted C4-C20 condensed polycyclic group, $R_4$, $R_5$, $R_6$, $R_7$ and $R_8$ are, each independently, hydrogen, a substituted or unsubstituted C1-C30 alkyl group, a substituted or unsubstituted C2-C30 alkenyl group, a substituted or unsubstituted C2-C30 alkynyl group, a substituted or unsubstituted C1-C30 alkoxy group, a substituted or unsubstituted C6-C30 aryloxy group, a substituted or unsubstituted C6-C30 aryl group, or a substituted or unsubstituted C4-C30 heteroaryl group.

According to another aspect of the present invention, there is provided an organic electroluminescent device comprising a first electrode, a second electrode, and an organic layer interposed between the first electrode and the second electrode, wherein the organic layer comprises the silicon-containing compound.

According to an embodiment of the present invention, the organic layer is selected from a hole injection layer, a hole transport layer, and a single layer (mono layer) having a hole injecting capability and a hole transporting capability.

According to another embodiment of the present invention, the organic layer is an emitting layer and a silicon-containing compound represented by Formula 1 is used as a fluorescent or phosphorescent host.

BRIEF DESCRIPTION OF THE DRAWINGS

A more complete appreciation of the invention, and many of the attendant advantages thereof, will be readily apparent as the same becomes better understood by reference to the following detailed description when considered in conjunction with the accompanying drawings in which like reference symbols indicate the same or similar components, wherein.

DETAILED DESCRIPTION OF THE INVENTION

Figure 1:
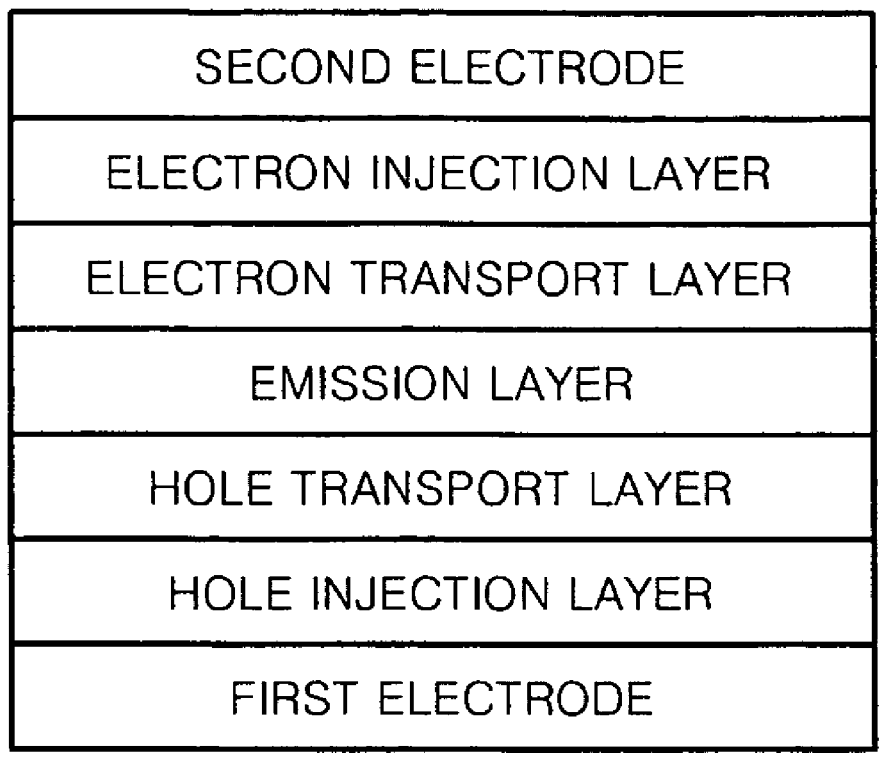
FIG. 1 is a schematic view of an organic electroluminescent device according to an embodiment of the present invention.

An aspect of the present invention is directed to a silicon-containing compound represented by Formula 1, wherein the silicon-containing compound has a carbazole group and a fluorenyl group. The silicon-containing compound may be used as an organic layer forming material of an organic electroluminescent device:

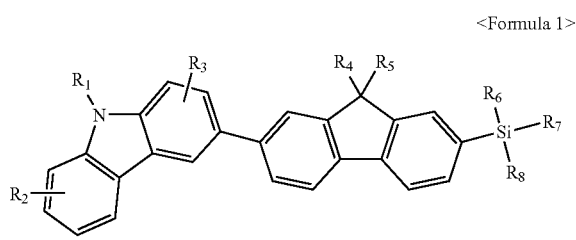

<Formula 1> wherein $R_1$ is a substituted or unsubstituted C1-C30 alkyl group, a substituted or unsubstituted C2-C30 alkenyl group, a substituted or unsubstituted C2-C30 alkynyl group, a substituted or unsubstituted C1-C30 alkoxy group, a substituted or unsubstituted C6-C30 aryloxy group, a substituted or unsubstituted C6-C30 aryl group, a substituted or unsubstituted C4-C20 heteroaryl group, or a substituted or unsubstituted C4-C30 condensed polycyclic group;

$R_2$ and $R_3$ are, each independently, hydrogen, fluorine, a cyano, amino, a substituted or unsubstituted C1-C30 alkyl group, a substituted or unsubstituted C2-C30 alkenyl group, a substituted or unsubstituted C2-C30 alkynyl group, a substituted or unsubstituted C1-C30 alkoxy group, a substituted or unsubstituted C6-C30 aryloxy group, a substituted or unsubstituted C6-C20 aryl group, a substituted or unsubstituted C4-C20 heteroaryl group, or a substituted or unsubstituted C4-C20 condensed polycyclic group; and $R_4$, $R_5$, $R_6$, $R_7$ and $R_8$ are, each independently, hydrogen, a substituted or unsubstituted C1-C30 alkyl group, a substituted or unsubstituted C2-C30 alkenyl group, a substituted or unsubstituted C2-C30 alkynyl group, a substituted or unsubstituted C1-C30 alkoxy group, a substituted or unsubstituted C6-C30 aryloxy group, a substituted or unsubstituted C6-C30 aryl group, or a substituted or unsubstituted C4-C30 heteroaryl group, and at least two adjacent groups selected from $R_4$, $R_5$, $R_6$, $R_7$ and $R_8$ may be optionally connected to form a saturated or unsaturated ring.

With regard to Formula 1, examples of the unsubstituted C1-C30 alkyl group include, but not limited to, methyl, ethyl, propyl, isobutyl, sec-butyl, pentyl, iso-amyl, hexyl, or the like. The substituted C1-C30 alkyl group is the C1-C30 alkyl group, wherein at least one hydrogen of the unsubstituted C1-C30 alkyl group atom is substituted with a substituent such as a halogen atom, a hydroxyl group, a nitro group, a cyano group, an amino group, an amidino group, hydrazine, hydrazone, a carboxyl group or salt thereof, a sulfuric acid or salt thereof, a phosphoric acid or salt thereof, a C1-C30 alkyl group, a C2-C30 alkenyl group, a C2-C30 alkynyl group, a C6-C30 aryl group, a C7-C20 arylalkyl group, a C2-C20 heteroaryl group, a C3-C30 heteroarylalkyl group, a C6-C30 aryloxy group, or a substituent represented by Formula —N($Z_1$)($Z_2$) wherein $Z_1$ and $Z_2$ may be each independently selected from the group consisting of hydrogen, a substituted or unsubstituted C1-C30 alkyl group, a substituted or unsubstituted C1-C30 haloalkyl group, a substituted or unsubstituted C6-C30 aryl group, a substituted or unsubstituted C6-C30 haloaryl group, and a substituted and unsubstituted C2-C30 heteroaryl group.

With regard to Formula 1, examples of the unsubstituted C1-C30 alkoxy group include, but not limited to, methoxy, ethoxy, cyclohexyloxy, isopropyloxy, or the like. The substituted C1-C30 alkoxy group is the C1-C30 alkoxy group, wherein at least one hydrogen atom of the unsubstituted C1-C30 alkoxy group is substituted with the substituents which have been described with the substituted C1-C30 alkyl groups described above.

With regard to Formula 1, examples of the unsubstituted C6-C30 aryloxy group include, but not limited to, phenyloxy, naphthyloxy, diphenyloxy, or the like. The substituted C6-C30 aryloxy group is the C6-C30 aryloxy group, wherein at least one hydrogen atom of the unsubstituted C6-C30 group is substituted with the substituents which have been described with the substituted C1-C30 alkyl groups described above.

With regard to Formula 1, the unsubstituted C6-C30 aryl group is an aromatic system having at least one aromatic ring and 6-30 carbon atoms, wherein when the number of aromatic rings included in the aromatic system is two or more, the aromatic rings may be fused or pendant to each other through, for example, a single bond. The substituted C6-C30 aryl group is the C6-C30 aryl group, wherein at least one hydrogen atom of the unsubstituted C6-C30 aryl group is substituted with the substituents which have been described with the substituted C1-C30 alkyl groups described above.

With regard to Formula 1, examples of the substituted or unsubstituted C6-C30 aryl group include a phenyl group, a C1-C10 alkyl phenyl group (for example, an ethylphenyl group), a halophenyl group (for example, o-, m- and p-fluorophenyl groups, or a dichlorophenyl group), a cyanophenyl group, a dicyanophenyl group, a trifluoromethoxyphenyl group, a biphenyl group, a halobiphenyl group, a cyanobiphenyl group, a C1-C10 alkyl biphenyl group, a C1-C10 alkoxy biphenyl group, o-, m-, and p-tolyl groups, o-, m- and p-kumenyl groups, a mesityl group, a phenoxyphenyl group, a (α,α-dimethylbenzene)phenyl group, a a(N,N'-dimethyl) aminophenyl group, a (N,N'-diphenyl)aminophenyl group, a pentalenyl group, an indenyl group, a naphthyl group, a halonaphthyl group (for example, a fluoronaphthyl group), a C1-C10 alkyl naphthyl group (for example, a methylnaphthyl group), a C1-C10 alkoxy naphthyl group (for example, a methoxynaphthyl group), a cyanonaphthyl group, an anthracenyl group, an azrenyl group, a heptarenyl group, an acenaphthylenyl group, a phenalenyl group, a fluorenyl group, an anthraquinolyl group, a methylanthryl group, a phenanthryl group, a triphenylene group, a pyrenyl group, a crecenyl group, an ethyl-crecenyl group, a picenyl group, a perilenyl group, a chloroperilenyl group, a pentaphenyl group, a pentacenyl group, a tetraphenylenyl group, a hexaphenyl group, a hexacenyl group, a rubicenyl group, a coronenyl group, a trinaphthylenyl group, a heptaphenyl group, a heptacenyl group, a pyranthrenyl group, and an ovalenyl group. In the substituted or unsubstituted C6-C30 aryl group, at least one hydrogen atom may be substituted with the substituents which have been described with the alkyl groups described above.

With regard to Formula 1, the unsubstituted C4-C20 heteroaryl group refers to a system including at least one aromatic ring, wherein the system has at least one hetero atom such as N, O, P and S and the other ring atoms all are carbons. When the number of aromatic rings included in the system is two or more, the aromatic rings may be fused or pendant to each other through, for example, a single bond. In the unsubstituted C4-C20 heteroaryl group, at least one hydrogen atom may be substituted with the substituents which have been described with the substituted C1-C30 alkyl groups described above.

With regard to Formula 1, examples of the unsubstituted C3-C30 heteroaryl group include a pyrazolyl group, an imidazolyl group, an oxazolyl group, a thiazolyl group, a triazolyl group, a tetrazolyl group, an oxadiazolyl group, a pyridinyl group, a pyridazinyl, a pyrimidinyl group, a triazinyl group, a carbazolyl group, an indolyl group, a quinolinyl group, and an isoquinolinyl group.

With regard to Formula 1, examples of the unsubstituted C4-C20 condensed polycyclic group include a pentalenyl group, a naphthyl group, an azrenyl group, a heptarenyl group, an acenaphthyl group, an anthryl group, a phenanthryl group, a quinolyl group, an anthraquinolyl group, a fluorenyl group, and a carbazolyl group. In the condensed polycyclic groups, at least one hydrogen atom may be substituted with the substituents which have been described with the alkyl groups described above.

According to an embodiment of the present invention, in consideration of manufacture, handling efficiency, and electrical characteristics, the compound represented by Formula 1 may be a compound represented by Formula 2:

[Formula 2]

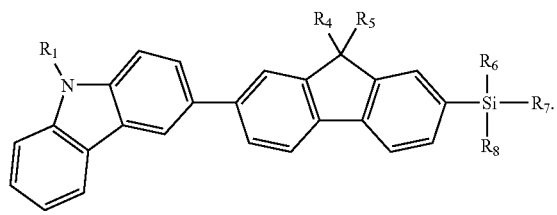

According to another embodiment of the present invention, in consideration of the manufacture, handling efficiency, and electrical characteristics of the final product, $R_1$ in Formula 1 may be selected from C1-C5 alkyl, phenyl, naphthyl, anthryl, biphenyl, terphenyl, fluorenyl, and pyridyl, wherein $R_1$ may be unsubstituted or substituted with C1-C5 alkyl, C1-C5 alkoxy, cyano, amine, halogen, phenoxy, phenyl, or pyridyl.

According to another embodiment of the present invention, in consideration of the manufacture, handling efficiency, and electrical characteristics, $R_4$ through $R_7$ in Formula 1 may be selected from C1-C5 alkyl and phenyl.

Among $R_4$, $R_5$, $R_6$, $R_7$ and $R_8$ in Formula 1, at least two adjacent substituents may be optionally connected to form a saturated or unsaturated ring. Specifically, $R_4$ and $R_5$ may be connected to each other to form cyclopentane or a spiro-type fluorine ring, and likewise, two substituents selected from $R_6$, $R_7$ and $R_8$ may from a saturated or unsaturated ring.

The compounds represented by Formula 1 according to an embodiment of the present invention may have a hole-injecting capability, a hole-transporting capability, and/or a light emitting capability. A compound that has carbazole and fluorine in its molecule as shown in the compound represented by Formula 1 has a high glass transition temperature (Tg) or a high melting point (Tm) due to introduction of the carbazole. Accordingly, when electroluminescence occurs, the compound has high heat resistance against Joule heat occurring in an organic layer, between organic layers, or between an organic layer and a metallic electrode and high durability in high-temperature environment. As described above, an organic electroluminescent device manufactured using the compound represented by Formula 1 according to an embodiment of the present invention has high durability during preservation and operation. In addition, since an organic film formed using the compound represented by Formula 1 according to an embodiment of the present invention has improved film characteristics due to introduction of the fluorene, characteristics of the organic electroluminescent device may be improved.

Examples of the silicon-containing compound represented by Formula 1 according to an embodiment of the present invention will now be described. Examples of the silicon-containing compound represented by Formula 1 include Compounds represented by Formulae 3 through 65 (hereinafter, which are also referred to as Compounds 1 through 63, respectively). However, the silicon-containing compound of the present invention is not limited to those compounds.

Formula 3

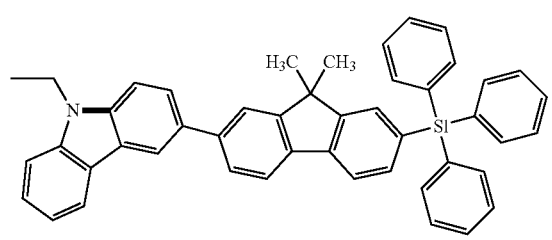

Formula 4

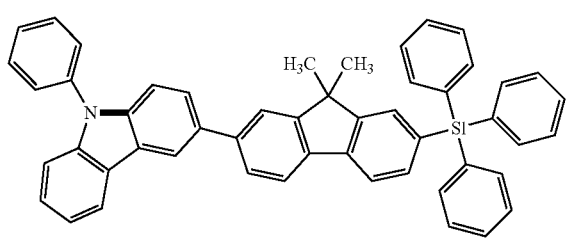

-continued
Formula 5
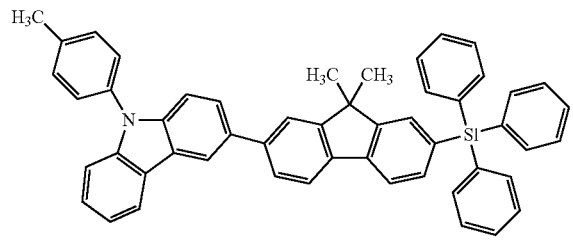
Formula 6
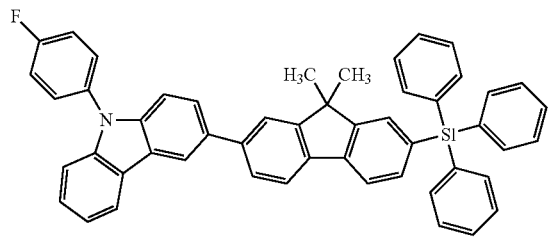
Formula 7
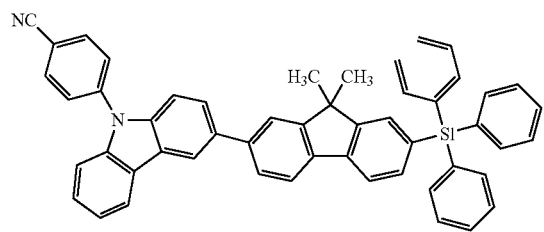
Formula 8
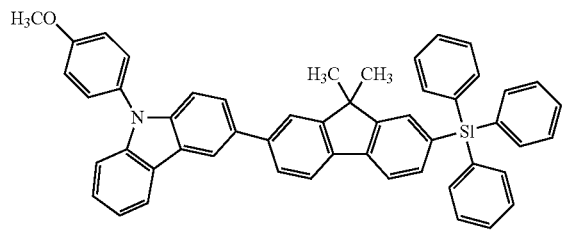
Formula 9
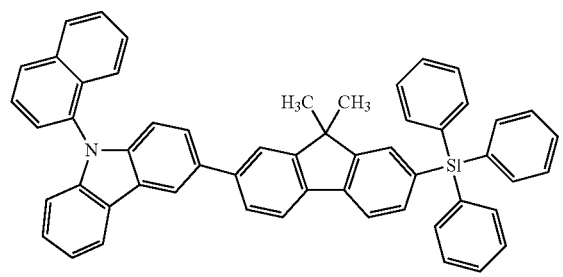
Formula 10
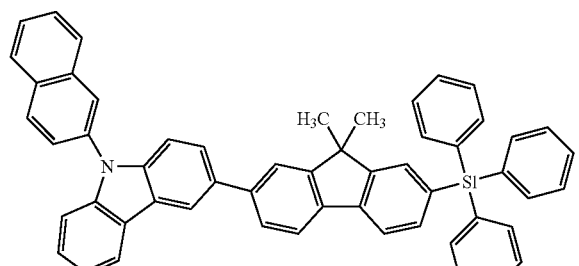
Formula 11
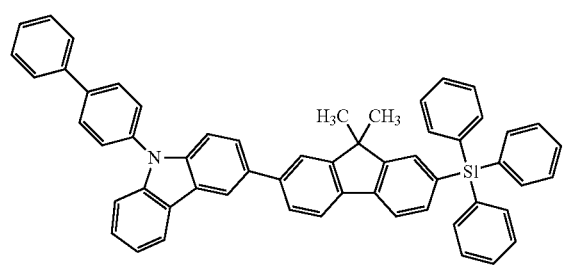
Formula 12
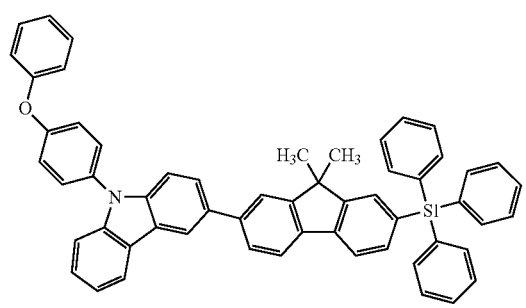
Formula 13
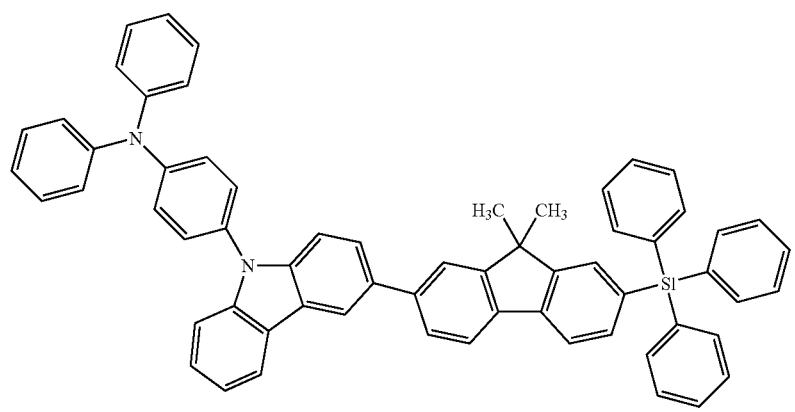

-continued
Formula 14
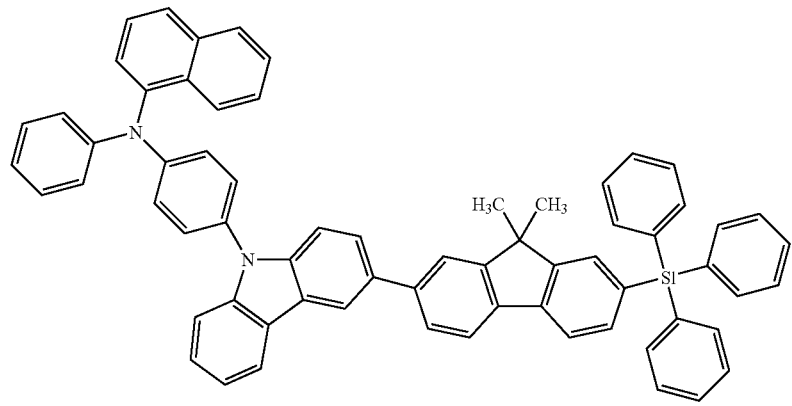
Formula 15
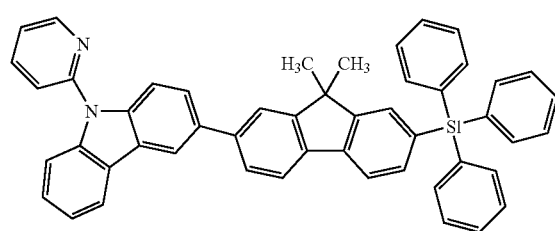
Formula 16
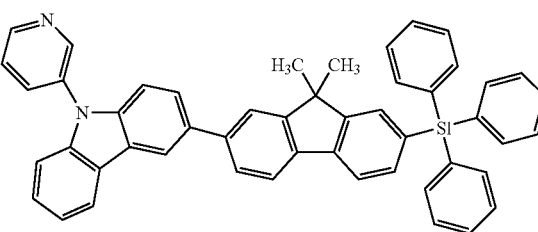
Formula 17
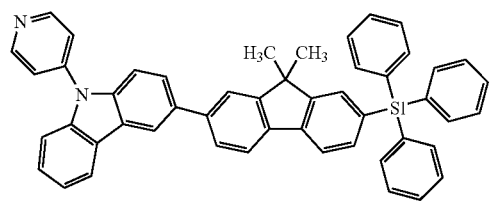
Formula 18
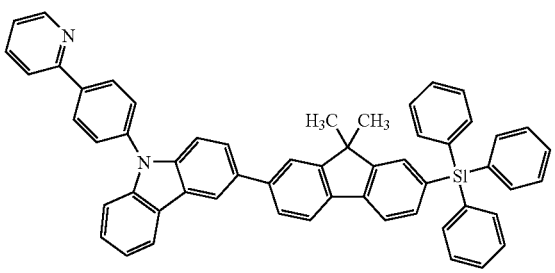
Formula 19
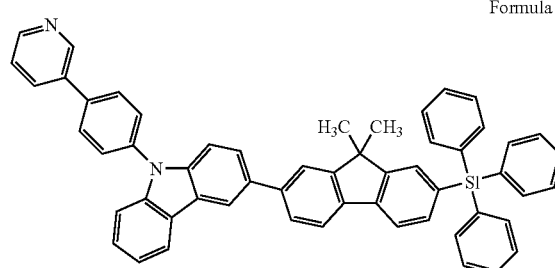
Formula 20
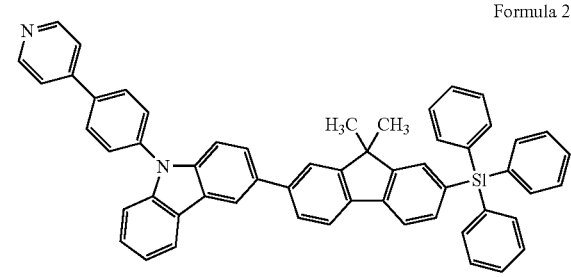
Formula 21
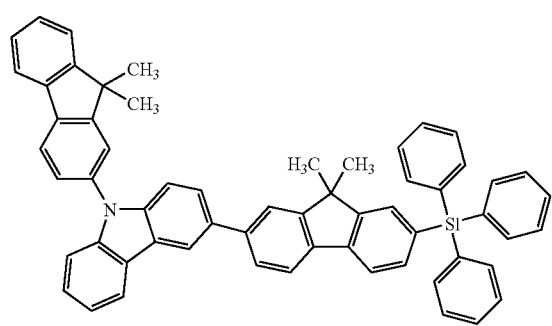
Formula 22
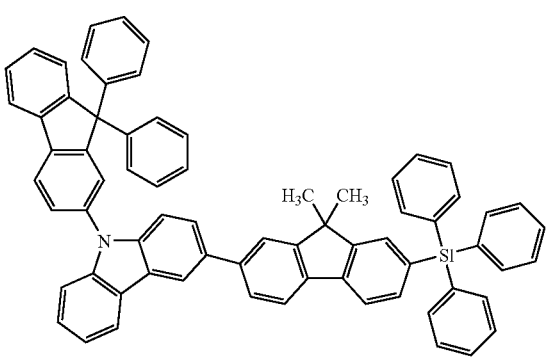

-continued
Formula 23
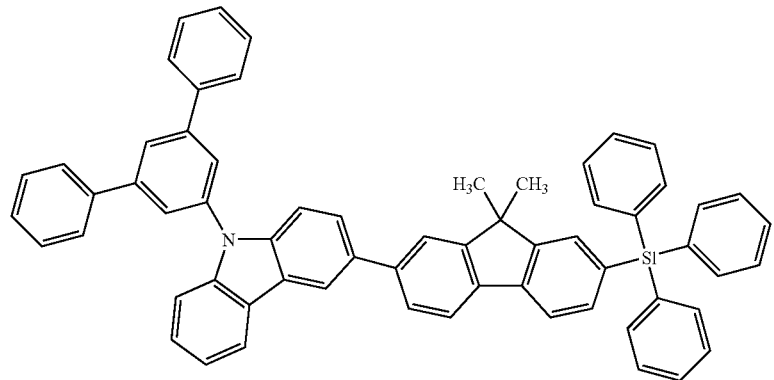
Formula 24
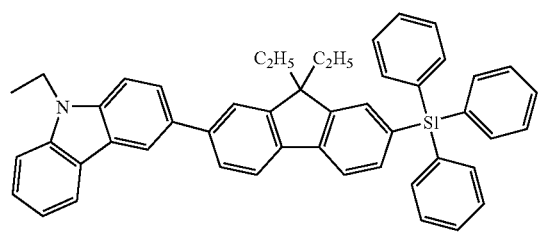
Formula 25
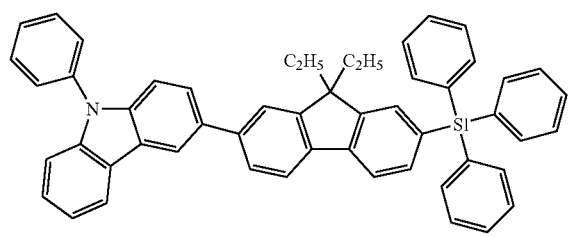
Formula 26
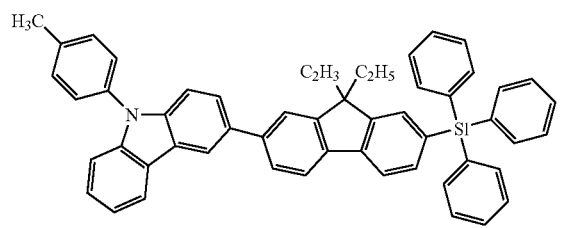
Formula 27
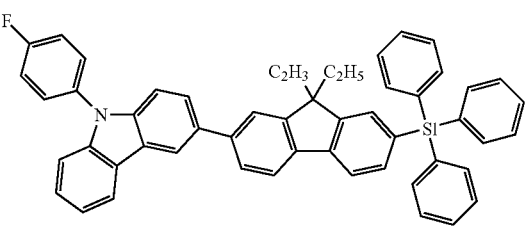
Formula 28
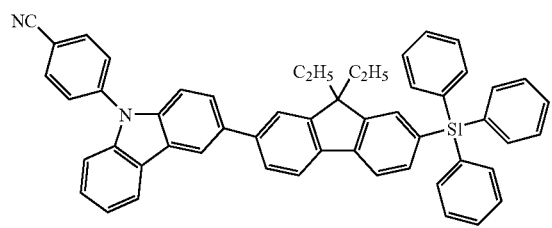
Formula 29
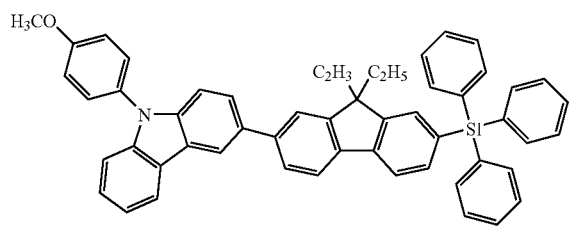
Formula 30
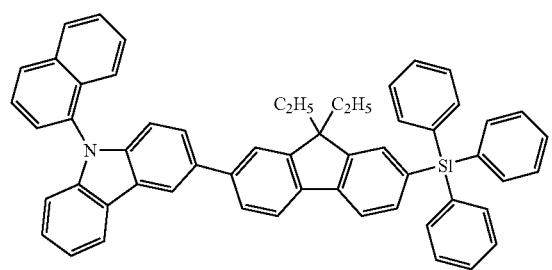
Formula 31
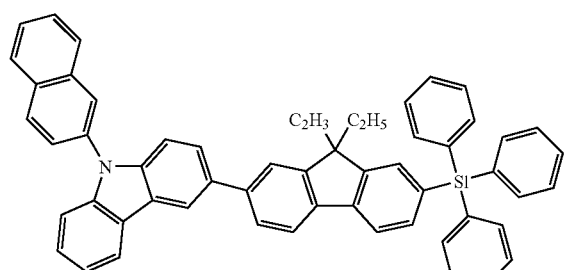

Formula 32
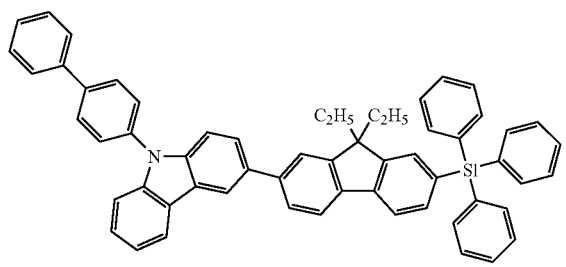
Formula 33
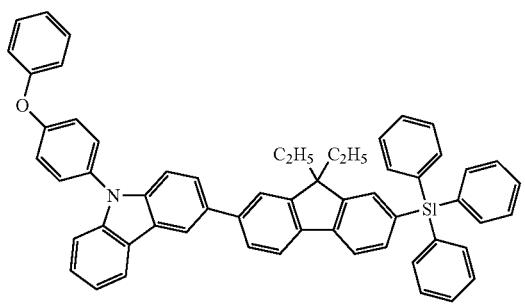
Formula 34
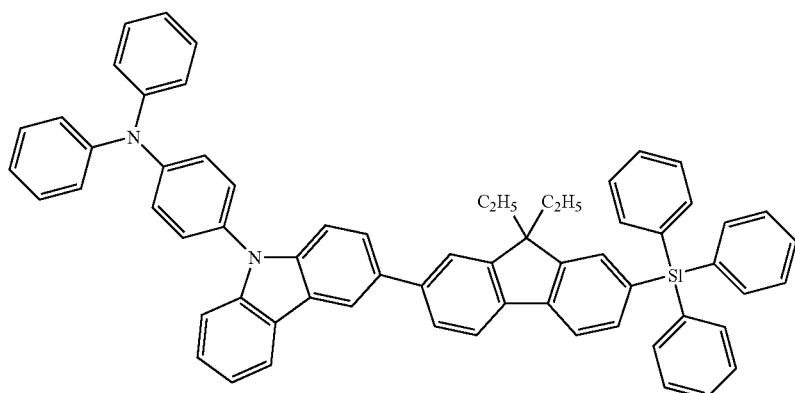
Formula 35
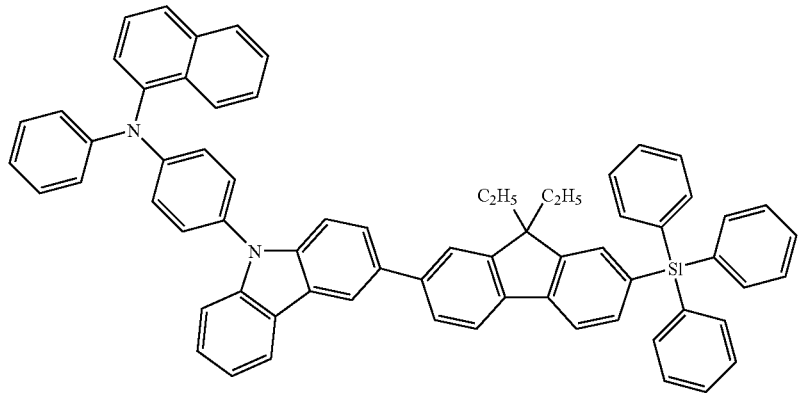
Formula 36
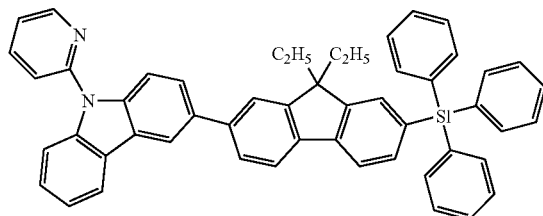
Formula 37
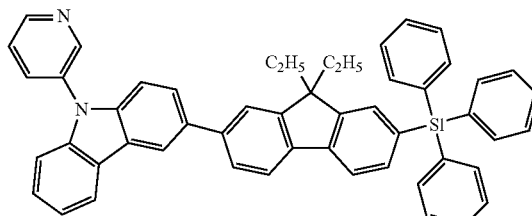
Formula 38
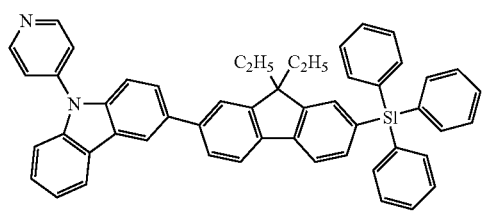
Formula 39
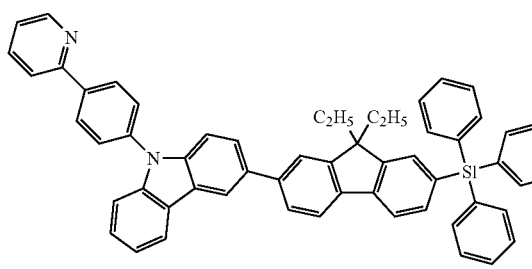

-continued
Formula 40
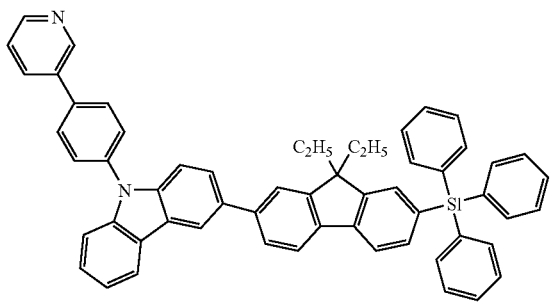
Formula 41
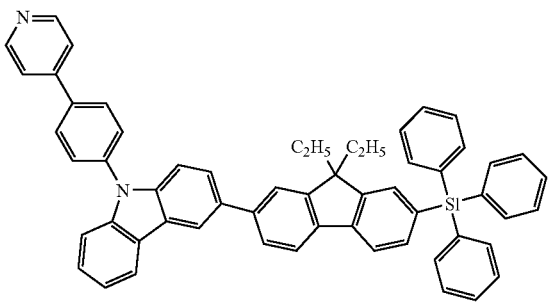
Formula 42
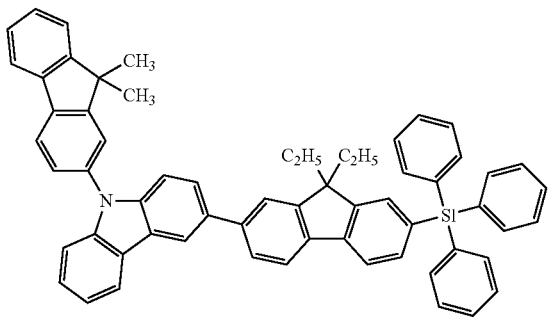
Formula 43
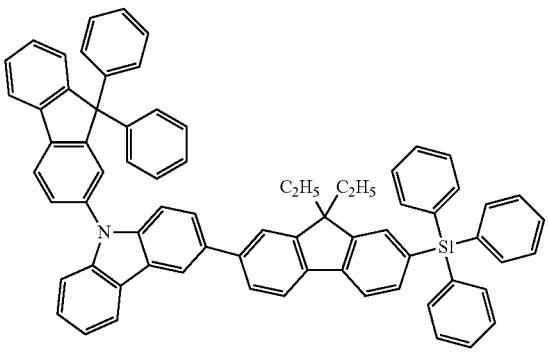
Formual 45
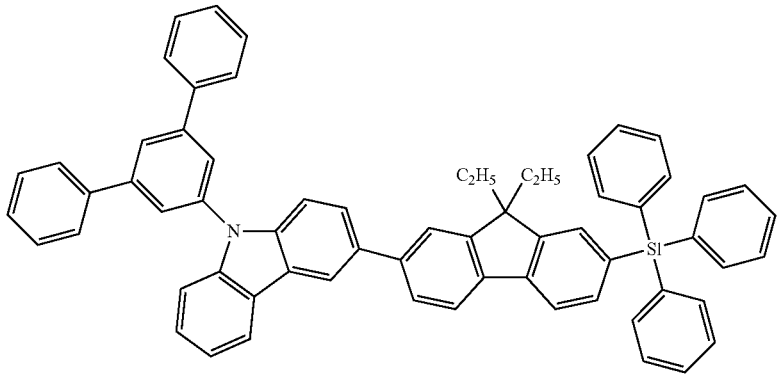
Formula 46
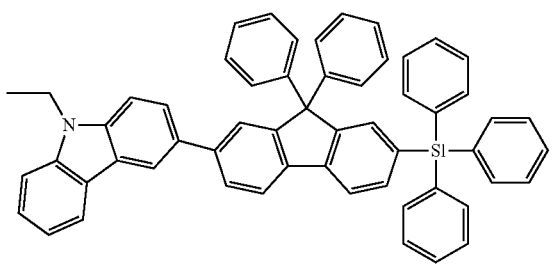
Formula 47
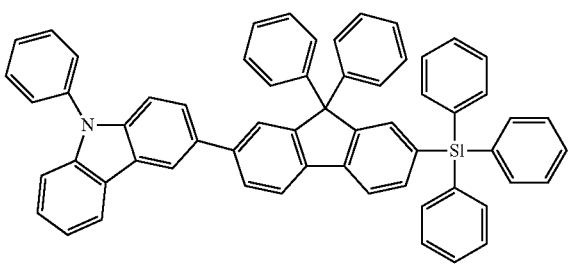
Formula 48
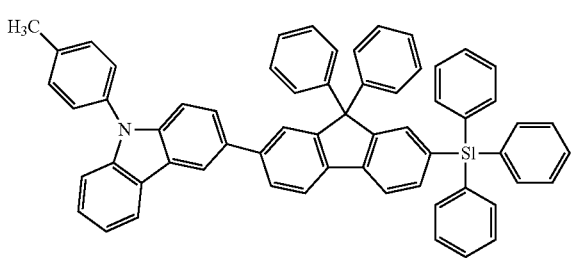
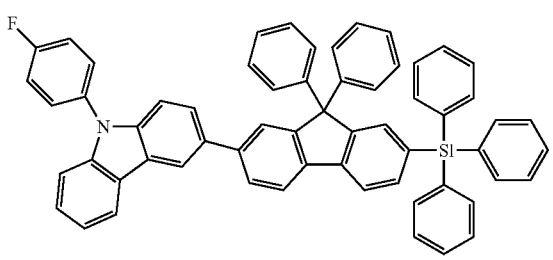

-continued
Formula 49
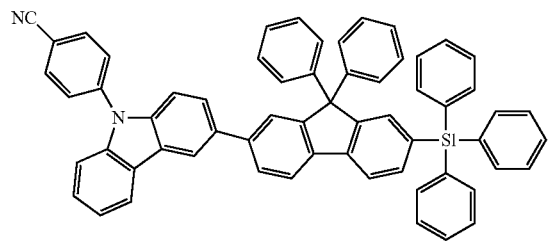
Formula 50
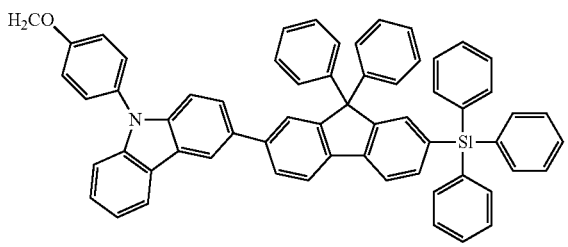
Formula 51
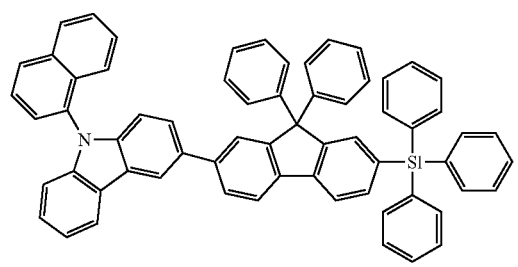
Formula 52
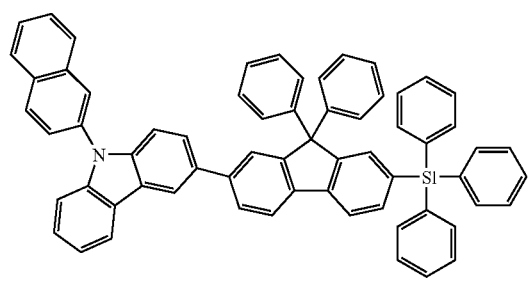
Formula 53
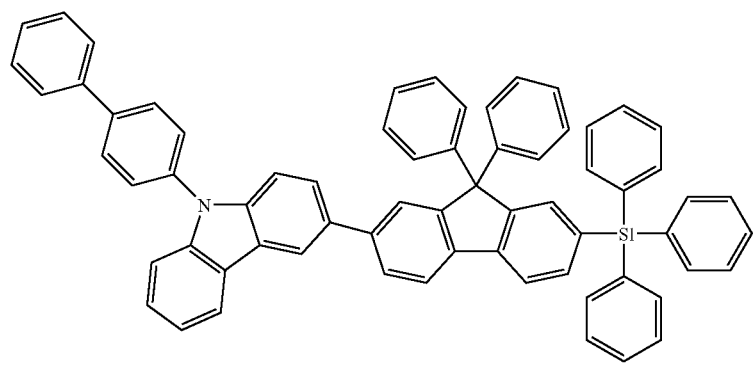
Formula 54
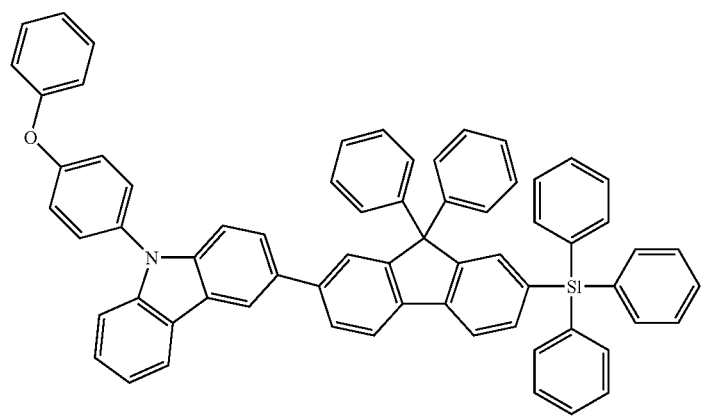

Formula 55
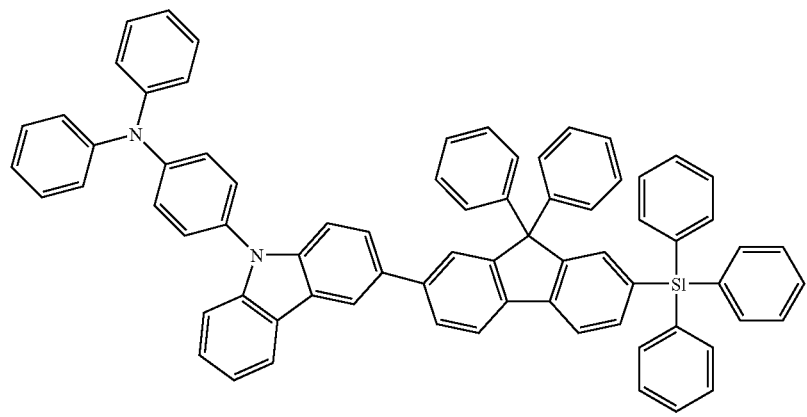
Formula 56
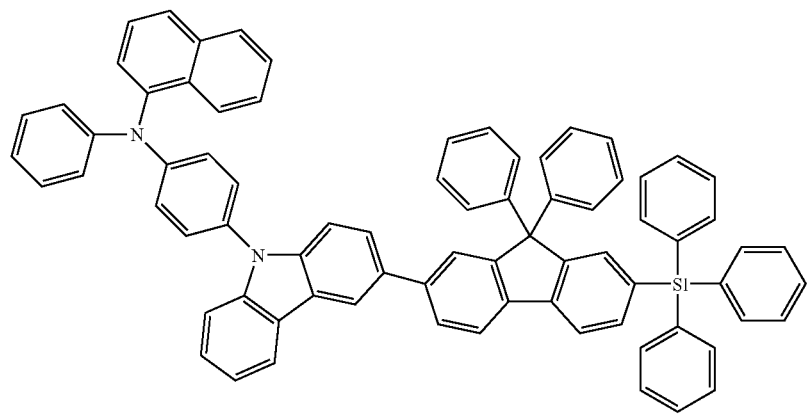
Formula 57
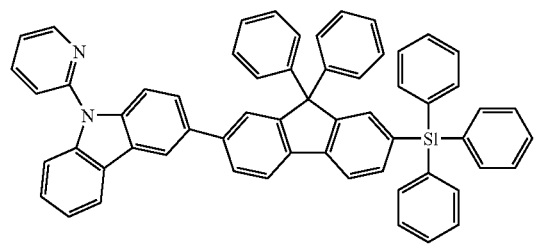
Formula 58
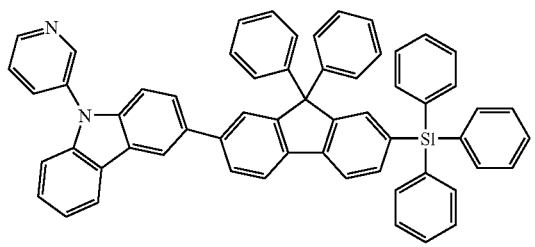
Formula 59
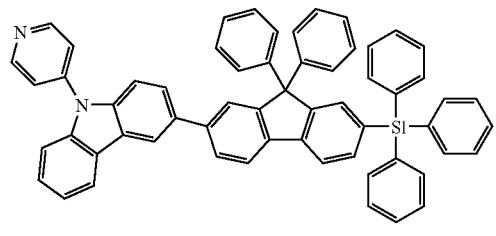
Formula 60
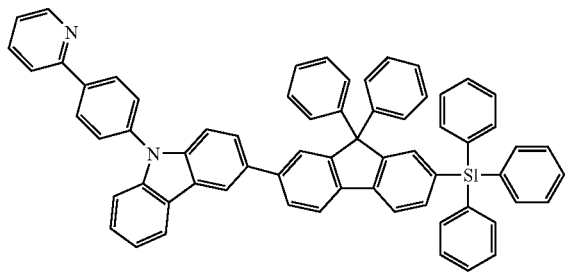

Formula 61

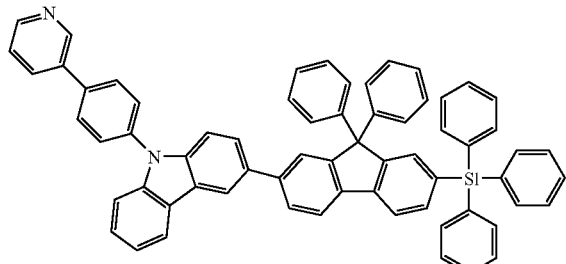

Formula 62

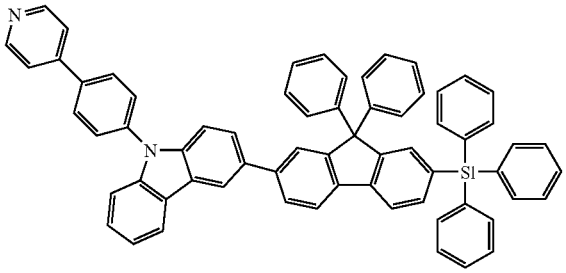

Formula 63

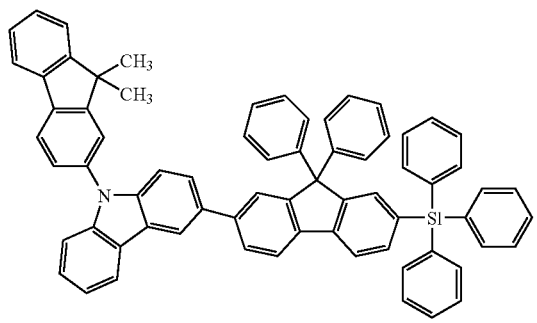

Formula 64

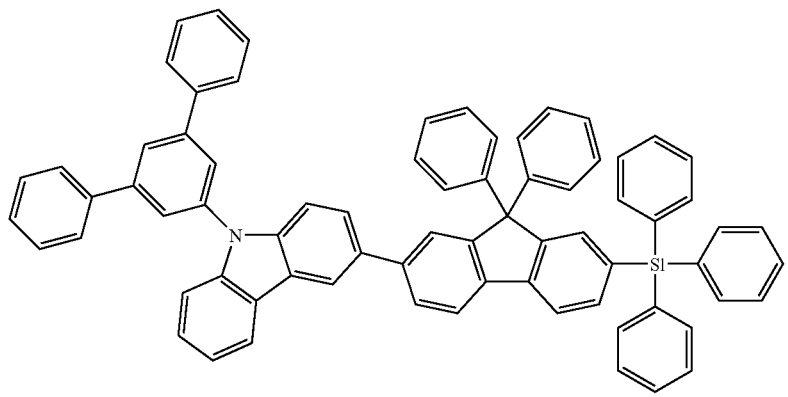

Formula 65

Another aspect of the present invention is directed to an organic electroluminescent device including a first electrode, a second electrode, and an organic layer interposed between the first electrode and the second electrode, wherein the organic layer includes the silicon-containing compound represented by Formula 1.

For the organic electroluminescent device according to the present invention, the organic layer including the silicon-containing compound represented by Formula 1 may be a hole injection layer, a hole transport layer, or a single layer having a hole injecting capability and a hole transporting capability. For example, the organic layer may be the hole transport layer. Also, the silicon-containing compound represented by Formula 1 may be used as a fluorescent or phosphorescent host of an emitting layer.

Meanwhile, the first electrode may be an anode and the second electrode may be a cathode, and otherwise, the first electrode may be a cathode and the second electrode may be an anode.

The organic electroluminescent device according to an embodiment of the present invention may be a bottom-emission type device having the stack structure of anode/hole injection layer(HIL)/hole transport layer(HTL)/emitting layer(EML)/electron transport layer(ETL)/electron injection layer(EIL)/cathode illustrated in FIG. 1. However, the structure of the organic electroluminescent device according to the present invention is not limited thereto and the organic electroluminescent device according to the present invention may also be a top-emission type device. If necessary, the organic electroluminescent device according to the present invention may further include one or two intermediate layers.

Specifically, an organic electroluminescent device according to an embodiment of the present invention may include a structure of first electrode/HIL/EMU/second electrode, a structure of first electrode/HIL/HTL/EML/ETL/second electrode or a structure of first electrode/HIL/HTL/ETL/ETL/EIL/second electrode. The organic electroluminescent device may also have a structure of first electrode/a single layer having a hole injecting capability and a hole transporting capability/EML/ETL/second electrode or a structure of first electrode/a single layer having a hole injecting capability and a hole transporting capability/EML/ETL/EIL/second electrode.

The compound represented by Formula 1 may be used as a hole injecting/transporting material having excellent hole injecting characteristics and hole transporting characteristics, specifically as a hole transporting material. In addition, the compound represented by Formula 1 may be used as a host material of blue, green, and red fluorescent and phosphorescent devices.

An organic electroluminescent device according to the present invention may be manufactured using various known methods. Accordingly, a method of manufacturing the organic electroluminescent device will not be described in the present specification The organic electroluminescent device according to the present invention may be included in various types of flat panel devices, such as passive matrix organic light emitting display devices or active matrix organic light emitting display devices. Specifically, when the organic electroluminescent device according to an embodiment of the present invention is used in active matrix organic light emitting display devices, the first electrode disposed on a substrate may function as a pixel electrode and may be electrically connected to a source electrode or drain electrode of a thin film transistor. In addition, the organic electroluminescent device according to an embodiment of the present invention may also be used in a flat panel apparatus that includes screens on both top and bottom sides.

Hereinafter, synthesis examples and examples of the silicon-containing compound represented by Formula 1 according to the present invention will be described in detail. However, the present invention will not be limited to those examples.

EXAMPLES

Synthesis Example 1

Synthesis of Intermediate 1

2.433 g (10 mmol) of phenylcarbazole was added to 100 mL of 80% acetic acid, and then 1.357 g (5.35 mmol) of iodine ($I_2$) and 0.333 g (1.46 mmol) of ortho-periodic acid ($H_5IO_6$) were added thereto in a solid state. The resultant mixture was stirred in a nitrogen atmosphere at 80 C for 2 hours.

After the reaction was finished, the reaction solution was extracted using 50 mL of ethylether three times. The collected organic layer was dried over magnesium sulfate ($MgSO_4$) and a solvent was evaporated to obtain the residue. The residue was refined by column chromatography and 3.23 g (yield 87%) of Intermediate 1 having the following structure was obtained. Intermediate 1 was a white solid:

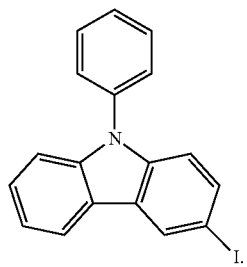

Intermediate 1

$^1$H NMR ($CDCl_3$, 300 MHz) δ (ppm)—8.43 (d, 1H), 8.05 (d, 1H), 7.62 (dd, 1H), 7.61-7.75 (m, 2H), 7.51-7.43 (m, 3H), 7.41-7.35 (m, 2H), 7.27 (dd, 1H), 7.14 (d, 1H)

Synthesis Example 2

Synthesis of Intermediate 2

Intermediate 2 having the following structure was prepared in the same manner as in Synthesis Example 1, except that naphthylcarbazole was used instead of phenylcarbazole. The yield of Intermediate 2 was 85%:

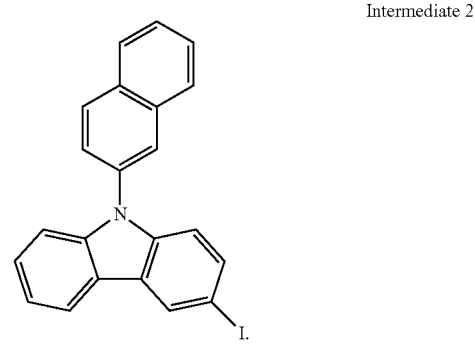

Intermediate 2

$^1$H NMR ($CDCl_3$, 300 MHz) δ (ppm)—8.29 (s, 1H), 8.13 (d, 1H), 7.92 (d, 1H), 7.80-7.73 (m, 3H), 7.59-7.49 (m, 5H), 7.37-7.29 (m, 3H)

Synthesis Example 3

Synthesis of Intermediate 3

Intermediate 3 having the following structure was prepared in the same manner as in Synthesis Example 1, except that biphenylcarbazole was used instead of phenylcarbazole. The yield of Intermediate 3 was 62%:

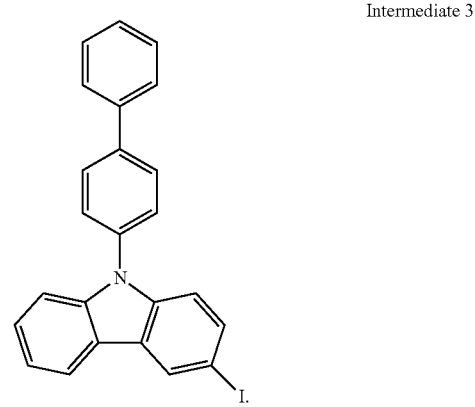

Intermediate 3

$^1$H NMR ($CDCl_3$, 300 MHz) δ (ppm)—8.30 (s, 1H), 8.13-8.11 (m, 1H), 7.74 (d, 1H), 7.59-7.53 (m, 3H), 7.40-7.28 (m, 8H), 6.64-6.60 (m, 2H)

Synthesis Example 4

Synthesis of Intermediate 4

17.6 g (50 mmol) of 2,7-dibromo-9,9-dimethylfluorene was dissolved in 150 mL of diethylether, and then normal butyllithium (20 mL, 2.5 M hexane solution) was added thereto while the temperature was maintained at −78 C. After 30 minutes, the temperature was slowly increased to room temperature. After 30 minutes, while a solution prepared by dissolving 23 mL (100 mmol) of triisopropylborate in 50 mL of diethylether was maintained at a temperature of −78 C, the mixed solution was slowly added thereto. The reaction solution was further stirred for 5 hours at room temperature and then washed with 200 mL of diethylether three times. The diethylether layer was collected and dried over magnesium sulfate and dried under a reduced pressure to obtain a product. The obtained product was recrystallized in normal hexane and 10.3 g (yield 65%) of Intermediate 4 having the following structure was obtained. Intermediate 4 was a while solid:

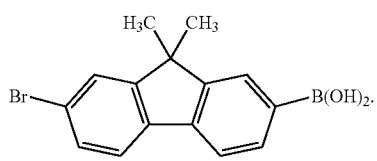

Intermediate 4

$^1$H NMR (CDCl$_3$, 400 MHz) δ (ppm)—8.09 (s, 2OH), 7.84-7.81 (dd, 1H), 7.75-7.72 (m, 2H), 7.67-7.65 (dd, 1H), 7.49-7.46 (dd, 1H), 7.40 (d, 1H), 1.85 (s, 6H)

Synthesis Example 5

Synthesis of Intermediate 5

Intermediate 5 having the following structure was prepared in the same manner as in Synthesis Example 4, except that 2,7-dibromo-9,9-diphenylfluorene was used instead of 2,7-dibromo-9,9-dimethylfluorene. The yield of Intermediate 5 was 58%:

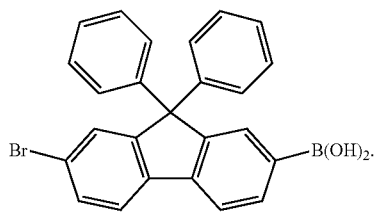

Intermediate 5

$^1$H NMR (CDCl$_3$, 400 MHz) δ (ppm)—8.27 (d, 1H), 8.09 (s, 2OH), 7.94-7.92 (dd, 1H), 7.81 (d, 1H), 7.74 (d, 1H), 7.69 (d, 1H), 7.60-7.51 (m, 5H), 7.18 (t, 4H), 7.02-6.97 (m, 2H)

Synthesis Example 6

Synthesis of Intermediate 6

9.51 g (30 mmol) of Intermediate 4, 16.6 g (60 mmol) of Intermediate 1, 1.7 g (1.5 mmol) of Pd(PPh$_3$)$_4$ and 20 g (150 mmol) of K$_2$CO$_3$ were dissolved in 100 mL of mixed solution of THF/H$_2$O (2:1) and then the resultant solution was stirred at 80° C. for 5 hours. The reaction solution was extracted with 600 mL of diethylether three times. The collected organic layer was dried over magnesium sulfate and the residue obtained by evaporating a solvent was re-crystallized with dichloromethane and normal hexane, thereby producing 10.03 g (yield 65%) of Intermediate 6 having the following structure:

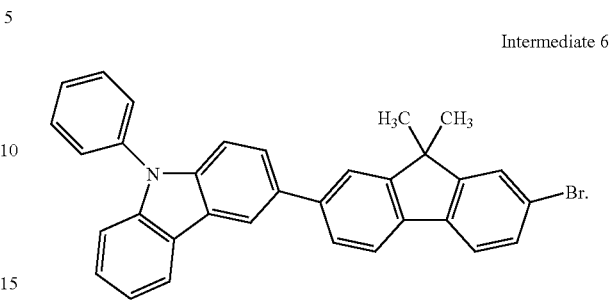

Intermediate 6

$^1$H NMR (CDCl$_3$, 400 MHz) δ (ppm)—8.16-8.14 (m, 1H), 7.94 (d, 1H), 7.68 (d, 1H), 7.63 (s, 1H), 7.50-7.46 (m, 5H), 7.36-7.27 (m, 5H), 7.07-6.94 (m, 4H), 1.85 (s, 6H)

$^{13}$C NMR (CDCl$_3$, 100 MHz) δ (ppm)—163.3, 150.7, 144.7, 144.2, 141.6, 141.0, 137.0, 136.0, 134.0, 131.8, 131.6, 129.8, 129.3, 129.2, 127.4, 127.1, 126.8, 126.3, 121.8, 121.2, 120.6, 120.4, 119.9, 119.5, 118.6, 115.4, 114.5, 109.0, 49.6, 24.5

Synthesis Example 7

Synthesis of Intermediate 7

Intermediate 7 having the following structure was synthesized in the same manner as in Synthesis Example 6, except that Intermediate 2 was used instead of Intermediate 1. The yield of Intermediate 7 was 63%:

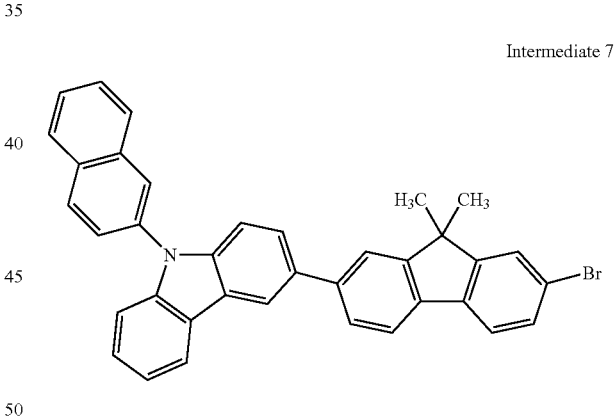

Intermediate 7

$^1$H NMR (CDCl$_3$, 400 MHz) δ (ppm)—8.15 (d, 1H), 7.95-7.91 (m, 2H), 7.81-7.46 (m, 9H), 7.36-7.27 (m, 4H), 7.06 (d, 1H), 7.00-6.94 (m, 4H), 1.85 (s, 6H)

$^{13}$C NMR (CDCl$_3$, 100 MHz) δ (ppm)—163.3, 150.7, 144.9, 144.2, 141.6, 140.0, 136.1, 136.0, 134.0, 131.8, 131.6, 129.5, 129.3, 129.2, 128.2, 127.9, 127.6, 126.8, 126.7, 126.2, 124.3, 122.5, 122.3, 121.8, 121.4, 121.2, 120.6, 119.9, 118.6, 117.3, 116.6, 114.5, 110.2, 105.1, 49.6, 24.5

Synthesis Example 8

Synthesis of Intermediate 8

Intermediate 8 having the following structure was synthesized in the same manner as in Synthesis Example 6, except that Intermediate 3 was used instead of Intermediate 1. The yield of Intermediate 8 was 58%:

Intermediate 8

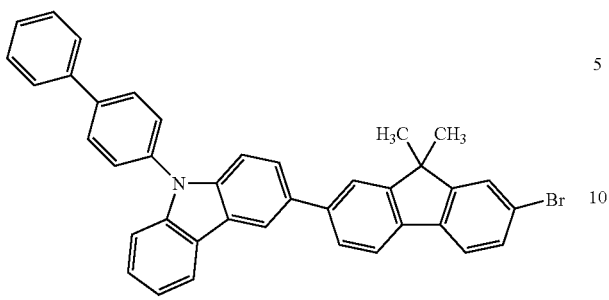

¹H NMR (CDCl₃, 400 MHz) δ (ppm)—8.16-8.14 (m, 1H), 7.95 (d, 1H), 7.69 (d, 1H), 7.63 (s, 1H), 7.60-7.56 (m, 2H), 7.49-7.45 (m, 1H), 7.41-7.27 (m, 9H), 7.07-6.94 (m, 4H), 6.64-6.60 (m, 2H), 1.85 (s, 6H)

¹³C NMR (CDCl₃, 100 MHz) δ (ppm)—163.3, 150.7, 144.2, 144.1, 141.6, 140.3, 139.3, 136.9, 136.0, 135.4, 134.0, 131.9, 131.8, 131.6, 129.3, 129.2, 128.9, 128.8, 127.2, 126.8, 126.3, 121.8, 121.2, 120.6, 120.4, 119.9, 119.5, 118.6, 116.8, 115.4, 114.5, 109.0, 49.6, 24.5

Synthesis Example 9

Synthesis of Intermediate 9

Intermediate 9 having the following structure was synthesized in the same manner as in Synthesis Example 6, except that Intermediate 5 was used instead of Intermediate 4. The yield of Intermediate 9 was 55%:

Intermediate 9

[structure]

¹H NMR (CDCl₃, 400 MHz) δ (ppm)—8.16-8.14 (m, 1H), 7.95 (d, 1H), 7.77 (d, 1H), 7.65-7.63 (m, 2H), 7.59 (dd, 1H); 7.52-7.46 (m, 9H), 7.37-7.27 (m, 4H), 7.20-7.13 (m, 5H), 7.06 (dd, 1H), 7.02-6.97 (m, 3H)

¹³C NMR (CDCl₃, 100 MHz) δ (ppm)—164.2, 151.5, 145.4, 144.7, 142.9, 141.0, 140.7, 137.0, 135.7, 135.1, 132.8, 131.3, 130.1, 129.8, 128.8, 127.8, 127.4, 127.1, 126.3, 126.0, 125.1, 122.9, 122.3, 121.7, 120.4, 119.9, 119.5, 118.6, 115.4, 114.1, 109.0, 72.9

Synthesis Example 10

Synthesis of Compound 2

5.14 g (10 mmol) of Intermediate 6 was dissolved in 30 mL of THF and then 4 mL (2.5M in Hexane) of butyllithium was added thereto at a temperature of −78 C. After one hour, 2.95 g (10 mmol) of chlorotriphenylsilane dissolved in 5 mL of THF at −78° C. was slowly added thereto. The resultant mixture was stirred at room temperature for 5 hours and then water was added thereto. The reaction solution was washed with 30 mL of diethylether three times. The diethylether layer was dried with magnesium sulfate and then dried under a reduced pressure to obtain a product. The product was refined by silica gel column chromatography to produce 4.16 g (yield 60%) of Compound 2 having the following structure. Compound 2 represented by Formula 4 was a while solid.

Formula 4

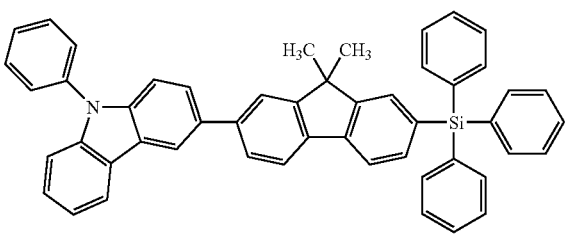

¹H NMR (CDCl₃, 400 MHz) δ (ppm)—8.66 (d, 1H), 8.30 (dd, 1H), 8.16-8.14 (m, 1H), 7.95 (d, 1H), 7.77 (d, 1H), 7.67-7.60 (m, 7H), 7.52-7.46 (m, 4H), 7.37-6.92 (m, 17H), 1.85 (s, 6H)

¹³C NMR (CDCl₃, 100 MHz) δ(ppm)—158.6, 146.9, 144.7, 141.5, 140.9, 139.5, 137.0, 136.4, 135.0, 134.0, 132.7, 132.3, 131.8, 130.2, 129.8, 129.6, 129.3, 127.9, 127.5, 127.4, 127.1, 126.8, 126.3, 120.4, 119.9, 119.5, 118.6, 118.0, 115.4, 114.5, 109.0, 49.6, 24.5

Synthesis Example 11

Synthesis of Compound 8

Compound 8 represented by Formula 10 was synthesized in the same manner as in Synthesis Example 10, except that Intermediate 7 was used instead of Intermediate 6. The yield of Compound 8 was 63%.

Formula 10

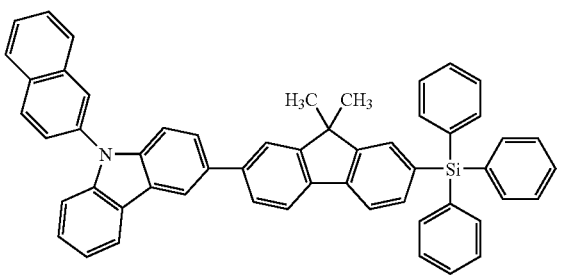

¹H NMR (CDCl₃, 400 MHz) δ (ppm)—8.66 (d, 1H), 8.30 (dd, 1H), 8.15 (d, 1H), 7.95-7.91 (m, 2H), 7.81-7.72 (m, 3H), 7.67-7.49 (m, 11H), 7.36-6.92 (m, 16H), 1.85 (s, 6H)

¹³C NMR (CDCl₃, 100 MHz) δ (ppm)—158.6, 146.9, 144.9, 141.5, 140.0, 139.5, 136.4, 136.1, 135.0, 134.0, 132.7, 132.3, 131.8, 130.2, 129.6, 129.5, 129.3, 128.2, 127.9, 127.6, 127.5, 126.8, 126.7, 126.2, 124.3, 122.5, 122.3, 121.4, 119.9, 118.6, 118.0, 117.3, 116.6, 114.5, 110.2, 105.1, 49.6, 24.5

Synthesis Example 12

Synthesis of Compound 9

Compound 9 represented by Formula 11 was synthesized in the same manner as in Synthesis Example 10, except that Intermediate 8 was used instead of Intermediate 6. The yield of Compound 9 was 61%.

Formula 11

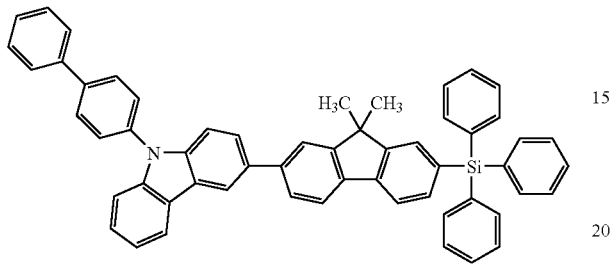

$^1$H NMR (CDCl$_3$, 400 MHz) δ (ppm)—8.66 (d, 1H), 8.30 (dd, 1H), 8.16-8.14 (m, 1H), 7.95 (d, 1H), 7.77 (d, 1H), 7.67-7.56 (m, 9H), 7.41-7.13 (m, 17H), 7.03-6.92 (m, 4H), 6.64-6.60 (m, 2H), 1.85 (s, 6H)

$^{13}$C NMR (CDCl$_3$, 100 MHz) δ (ppm)—158.6, 146.9, 144.1, 141.5, 140.3, 139.5, 139.3, 136.9, 136.4, 135.4, 135.0, 134.0, 132.7, 132.3, 131.9, 131.8, 130.2, 129.6, 129.3, 128.9, 128.8, 127.9, 127.5, 127.2, 126.8, 126.3, 120.4, 119.9, 119.5, 118.6, 118.0, 116.8, 115.4, 114.5, 109.0, 49.6, 24.5

Synthesis Example 13

Synthesis of Compound 44

Compound 44 represented by Formula 46 was synthesized in the same manner as in Synthesis Example 10, except that Intermediate 9 was used instead of Intermediate 6. The yield of Compound 44 was 57%.

Formula 46

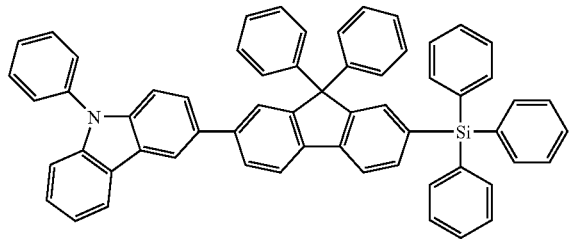

$^1$H NMR (CDCl$_3$, 400 MHz) δ (ppm)—9.29 (d, 1H), 8.41 (dd, 1H), 8.16-8.14 (m, 1H), 7.95 (d, 1H), 7.85 (d, 1H), 7.67-7.60 (m, 7H), 7.52-6.97 (m, 31H)

$^{13}$C NMR (CDCl$_3$, 100 MHz) δ (ppm)—159.5, 147.8, 144.7, 142.8, 141.0, 140.7, 140.6, 137.0, 136.4, 136.0, 135.9, 135.1, 132.8, 132.2, 132.0, 131.3, 129.8, 129.6, 128.8, 127.9, 127.8, 127.4, 127.2, 127.1, 126.3, 126.1, 126.0, 125.1, 120.4, 119.9, 119.5, 119.2, 118.6, 115.4, 114.1, 109.0, 72.9

Example 1

To produce an anode, a corning 15 Ω/cm$^2$ (1200 Å) ITO glass substrate was cut to a size of 50 mm×50 mm×0.7 mm and then sonicated in isopropyl alcohol and pure water each for five minutes, and then cleaned by irradiation of ultraviolet rays for 30 minutes and exposure to ozone. The resultant glass substrate was mounted on a vacuum deposition device.

Then, first, 2-TNATA that is a known HIL forming material was vacuum-deposited on the glass substrate to form a HIL having a thickness of 600 Å, and then Compound 2 as a hole transporting compound was vacuum deposited on the HIL to form a HTL having a thickness of 300 Å.

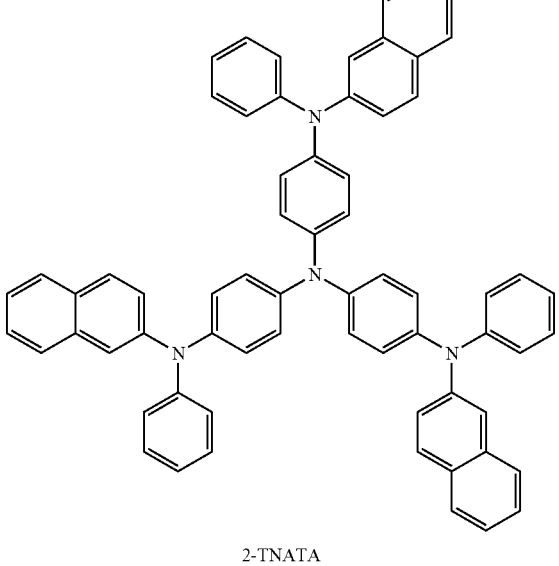

2-TNATA

On the HTL, tri-8-quinolinolatoaluminum (Alq$_3$) that is a known green fluorescent host and 10-(2-Benzothiazolyl)-2, 3,6,7-tetrahydro-1,1,7,7-tetramethyl-1H,5H,11H-(1)-benzopyropyrano(6,7-8-i,j)quinolizin-11-one (C545T) that is a known green fluorescent dopant were simultaneously deposited in a weight ratio of 98:2 to form an EML having a thickness of 300 Å.

Then, Alq$_3$ was deposited on the EML to form an ETL having a thickness of 300 Å, and then LiF that is halogenated alkali metal was deposited on the ETL to form an EIL having a thickness of 10 Å and Al was deposited on the EIL to form a cathode having a thickness of 3,000 Å, thereby forming an LiF/Al electrode. As a result, an organic electroluminescent device was manufactured.

The organic electroluminescent device had a driving voltage of 6.8 V, luminosity of 7,733 cd/m$^2$, a color coordinate of (0.310, 0.644), and a luminescent efficiency of 15.46 cd/A, at the current density of 50 mA/cm$^2$.

Example 2

An organic electroluminescent device was manufactured in the same manner as in Example 1, except that the HIL was formed using Compound 8 instead of Compound 2.

The organic electroluminescent device had a driving voltage of 6.86 V, luminosity of 7,868 cd/m$^2$, a color coordinate of (0.309, 0.641), and a luminescent efficiency of 15.74 cd/A, at the current density of 50 mA/cm$^2$.

Example 3

An organic electroluminescent device was manufactured in the same manner as in Example 1, except that the HTL was formed using Compound 9 instead of Compound 2.

The organic electroluminescent device had a driving voltage of 6.73 V, luminosity of 8,026 cd/m$^2$, a color coordinate of (0.309, 0.643), and a luminescent efficiency of 16.05 cd/A, at the current density of 50 mA/cm$^2$.

Example 4

An organic electroluminescent device was manufactured in the same manner as in Example 1, except that the HIL was formed using Compound 44 instead of Compound 2.

The organic electroluminescent device had a driving voltage of 7.13 V, luminosity of 7,434 cd/m$^2$, a color coordinate of (0.310, 0.642), and a luminescent efficiency of 14.87 cd/A, at the current density of 50 mA/cm$^2$.

Comparative Example 1

An organic electroluminescent device was manufactured in the same manner as in Example 1, except that the HTL was formed using known 4,4'-bis[N-(1-naphthyl)-N-phenylamino]biphenyl (NPB) instead of Compound 2.

The organic electroluminescent device had a driving voltage of 7.45 V at the current density of 50 mA/cm$^2$, luminosity of 6,102 cd/m$^2$, a color coordinate of (0.309, 0.642), and a luminescent efficiency of 12.2 cd/A.

Figure 2:
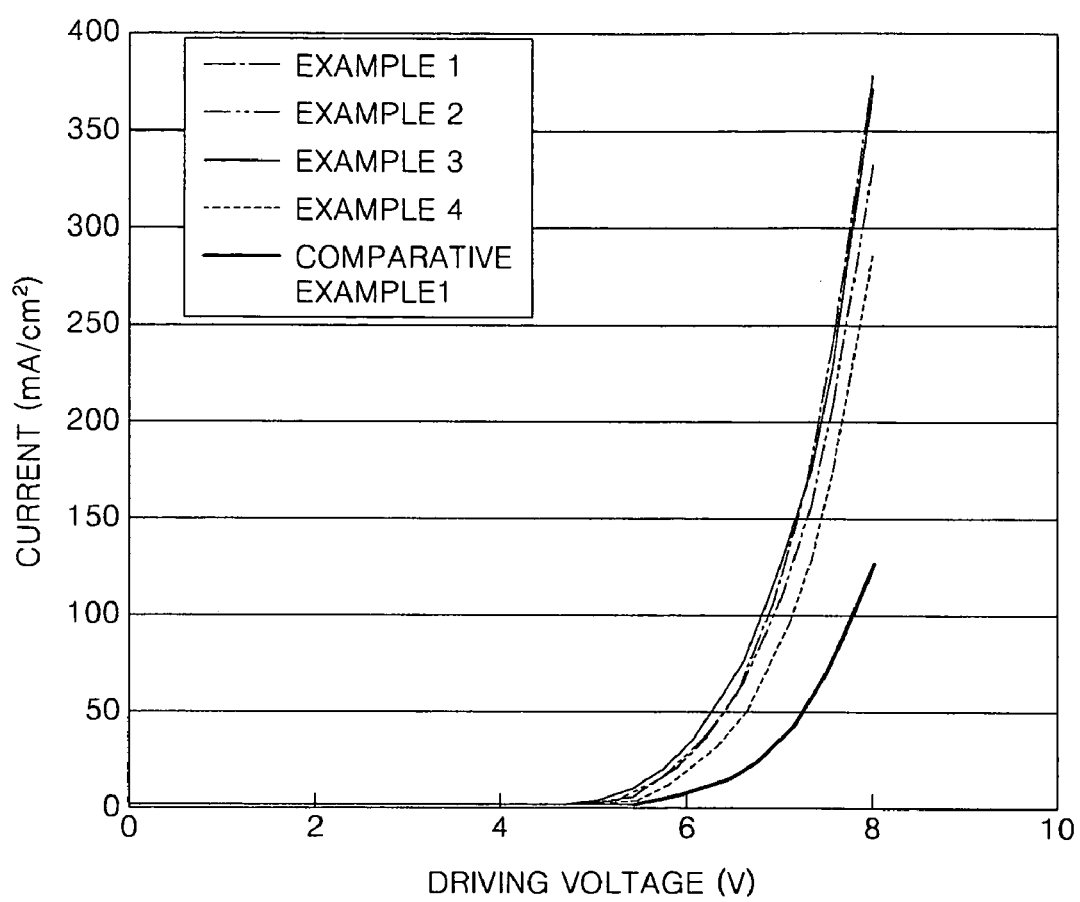
FIG. 2 is a graph showing current density characteristics of organic electroluminescent devices prepared according to Examples 1-4 and Comparative Example 1.

For the organic electroluminescent devices manufactured using silicon-containing compounds represented by Formula 1 according to the embodiments of the present invention, the driving voltage was lower than when NPB was used. In addition, the organic electroluminescent devices manufactured using silicon-containing compounds represented by Formula 1 according to the embodiments of the present invention had significantly high efficiency and showed excellent I-V-L characteristics (see FIG. 2). Organic electroluminescent devices manufactured using compounds according to the present invention having an excellent hole injecting capability and hole transporting capability had a low driving voltage, a high efficiency, high luminosity, and a long lifetime.

Since a silicon-containing compound represented by Formula 1 has excellent electrical characteristics and a charge transporting capability, the silicon-containing compound can be used as a hole injecting material, a hole transporting material, and/or a light emitting material that are suitable for all-color fluorescent and phosphorescent organic light emitting devices such as red, green, blue, and white fluorescent and phosphorescent organic light emitting devices. When the silicon-containing compound is used to manufacture an organic electroluminescent device, the organic electroluminescent device has a high efficiency, a low driving voltage, high luminosity, and a long lifetime.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A silicon-containing compound represented by Formula 1:

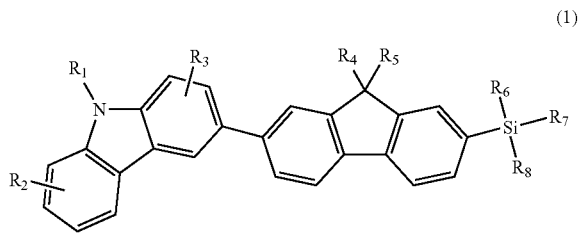

wherein $R_1$ is selected from a substituted or unsubstituted C1-C30 alkyl group, a substituted or unsubstituted C2-C30 alkenyl group, a substituted or unsubstituted C2-C30 alkynyl group, a substituted or unsubstituted C1-C30 alkoxy group, a substituted or unsubstituted C6-C30 aryloxy group, a substituted or unsubstituted C6-C30 aryl group, a substituted or unsubstituted C4-C20 heteroaryl group, and a substituted or unsubstituted C4-C30 condensed polycyclic group;

$R_2$ and $R_3$ are, each independently, hydrogen, fluorine, a cyano, amino, a substituted or unsubstituted C1-C30 alkyl group, a substituted or unsubstituted C2-C30 alkenyl group, a substituted or unsubstituted C2-C20 alkynyl group, a substituted or unsubstituted C1-C30 alkoxy group, a substituted or unsubstituted C6-C30 aryloxy group, a substituted or unsubstituted C6-C20 aryl group, a substituted or unsubstituted C4-C20 heteroaryl group, or a substituted or unsubstituted C4-C20 condensed polycyclic group; and $R_4$, $R_5$, $R_6$, $R_7$ and $R_8$ are, each independently, hydrogen, a substituted or unsubstituted C1-C30 alkyl group, a substituted or unsubstituted C2-C30 alkenyl group, a substituted or unsubstituted C2-C30 alkynyl group, a substituted or unsubstituted C1-C30 alkoxy group, a substituted or unsubstituted C6-C30 aryloxy group, a substituted or unsubstituted C6-C30 aryl group, or a substituted or unsubstituted C4-C30 heteroaryl group.

2. An organic electroluminescent device comprising a first electrode, a second electrode, and an organic layer interposed between the first electrode and the second electrode, the organic layer selected from the group consisting of a hole injection layer, a hole transport layer, and a monolayer having a hole injecting capability and a hole transporting capability, the organic layer comprising the silicon-containing compound of claim 1.

3. An organic electroluminescent device, comprising:

a first electrode;

a second electrode; and an organic layer interposed between the first electrode and the second electrode, the organic layer comprising a silicon-containing compound represented by Formula 1:

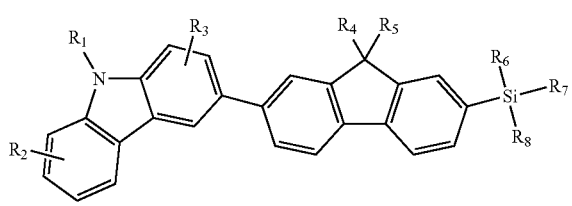

(1)

wherein $R_1$ is selected from a substituted or unsubstituted C1-C30 alkyl group, a substituted or unsubstituted C2-C30 alkenyl group, a substituted or unsubstituted C2-C30 alkynyl group, a substituted or unsubstituted C1-C30 alkoxy group, a substituted or unsubstituted C6-C30 aryloxy group, a substituted or unsubstituted C6-C30 aryl group, a substituted or unsubstituted C4-C20 heteroaryl group, and a substituted or unsubstituted C4-C30 condensed polycyclic group;

$R_2$ and $R_3$ are, each independently, hydrogen, fluorine, a cyano, amino, a substituted or unsubstituted C1-C30 alkyl group, a substituted or unsubstituted C2-C30 alkenyl group, a substituted or unsubstituted C2-C20 alkynyl group, a substituted or unsubstituted C1-C30 alkoxy group, a substituted or unsubstituted C6-C30 aryloxy group, a substituted or unsubstituted C6-C20 aryl group, a substituted or unsubstituted C4-C20 heteroaryl group, or a substituted or unsubstituted C4-C20 condensed polycyclic group; and $R_4$, $R_5$, $R_6$, $R_7$ and $R_8$ are, each independently, hydrogen, a substituted or unsubstituted C1-C30 alkyl group, a substituted or unsubstituted C2-C30 alkenyl group, a substituted or unsubstituted C2-C30 alkynyl group, a substituted or unsubstituted C1-C30 alkoxy group, a substituted or unsubstituted C6-C30 aryloxy group, a substituted or unsubstituted C6-C30 aryl group, or a substituted or unsubstituted C4-C30 heteroaryl group.

4. The organic electroluminescent device of claim 3, wherein the organic layer comprises at least one of a hole injection layer and a hole transport layer, and the silicon-containing compound represented by Formula 1 is included in said at least one of the hole injection layer and the hole transport layer.

5. The organic electroluminescent device of claim 3, wherein the organic layer comprises a monolayer having both a hole injecting capability and a hole transporting capability, and the silicon-containing compound represented by Formula 1 is included in said monolayer.

6. The organic electroluminescent device of claim 3, wherein the organic layer comprises an emitting layer, and the silicon-containing compound is used as a fluorescent or phosphorescent host in the emitting layer.

7. The organic electroluminescent device of claim 3, wherein at least two adjacent substituents selected from the group consisting of $R_4$, $R_5$, $R_6$, $R_7$ and $R_8$ are connected to form a saturated or unsaturated ring.

8. The organic electroluminescent device of claim 3, wherein the silicon-containing compound represented by Formula 1 is a compound represented by Formula 2:

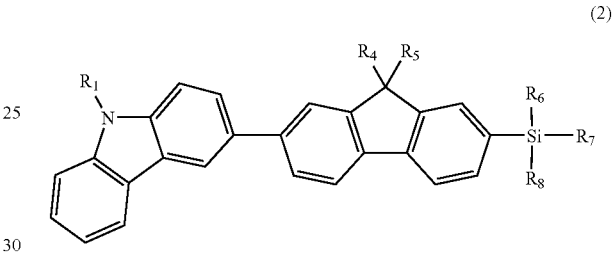

(2)

wherein $R_1$, $R_4$, $R_5$, $R_6$, $R_7$ and $R_8$ are as defined in claim 3.

9. The organic electroluminescent device of claim 3, wherein $R_1$ is selected from the group consisting of C1-C5 alkyl, phenyl, naphthyl, anthryl, biphenyl, terphenyl, fluorenyl, and pyridyl, wherein $R_1$ is unsubstituted or substituted with C1-C5 alkyl, C1-C5 alkoxy, cyano, amine, halogen, phenoxy, phenyl, or pyridyl; and $R_4$ through $R_7$ are, each independently, C1-C5 alkyl or phenyl.

10. The organic electroluminescent device of claim 3, wherein the silicon-containing compound is represented by one of the following structures:

Formula 3

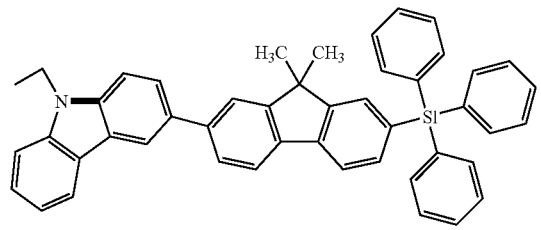

Formula 4

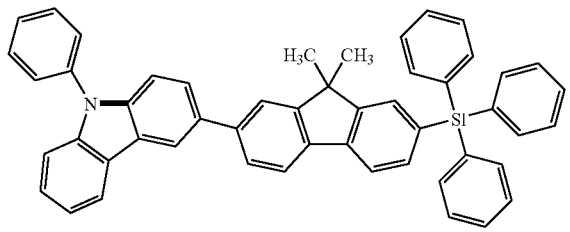

Formula 5

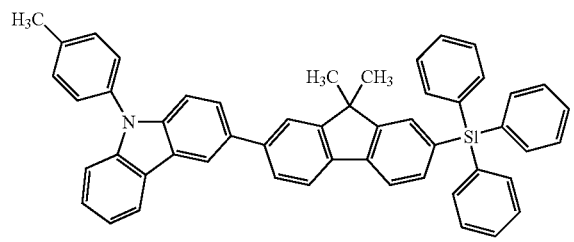

Formula 6

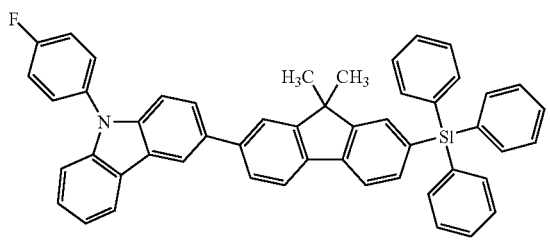

-continued
Formula 7
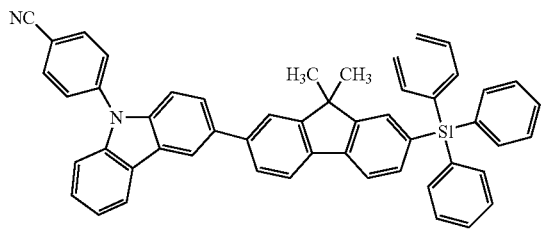
Formula 8
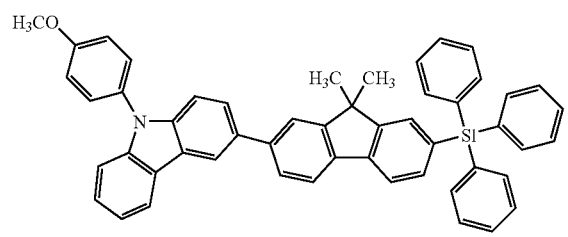
Formula 9
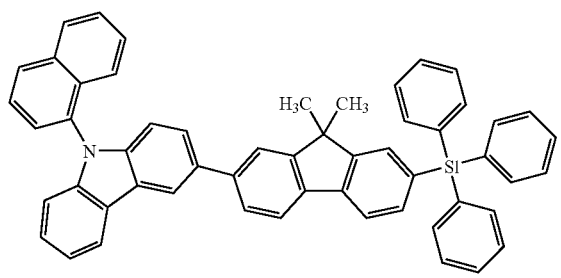
Formula 10
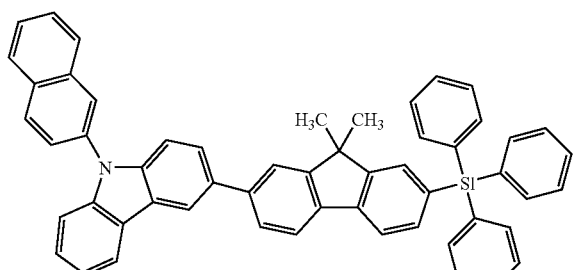
Formula 11
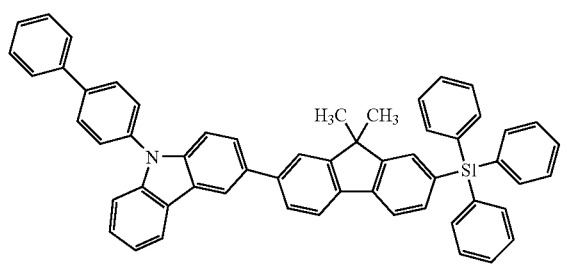
Formula 12
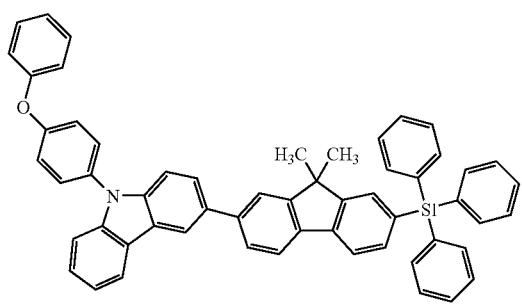
Formula 13
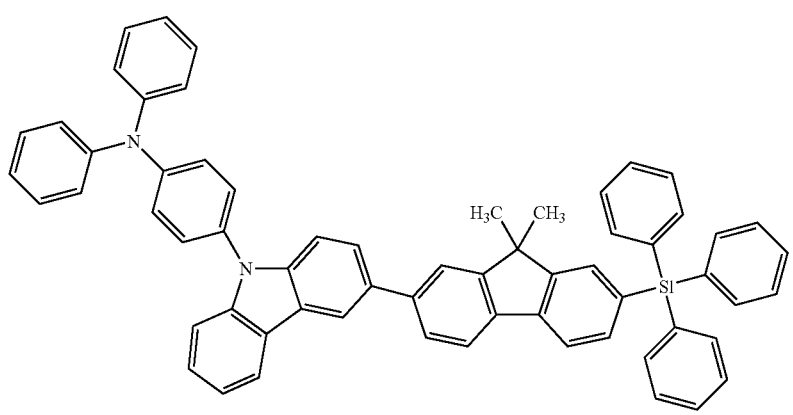

-continued
Formula 14
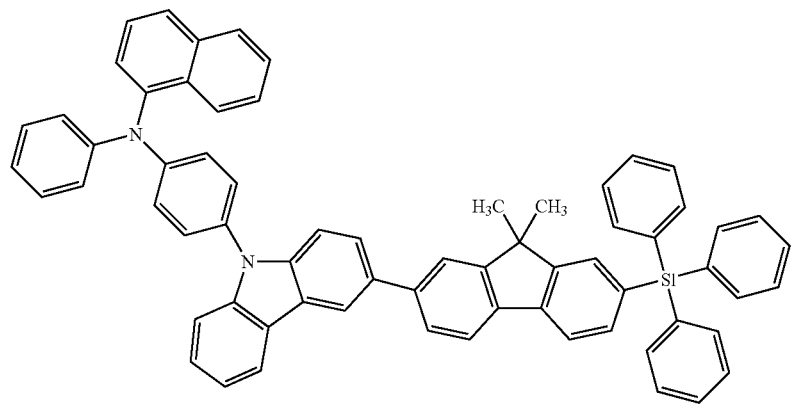
Formula 15
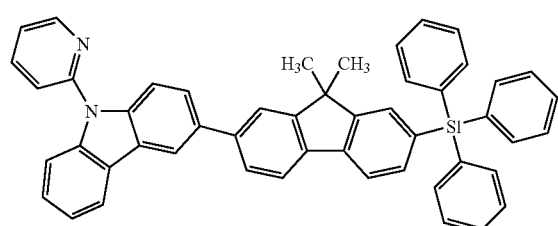
Formula 16
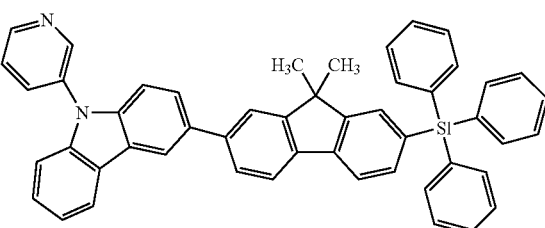
Formula 17
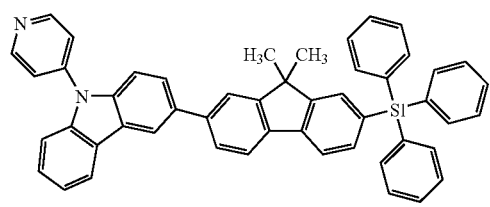
Formula 18
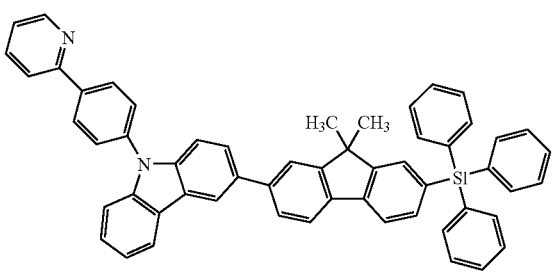
Formula 19
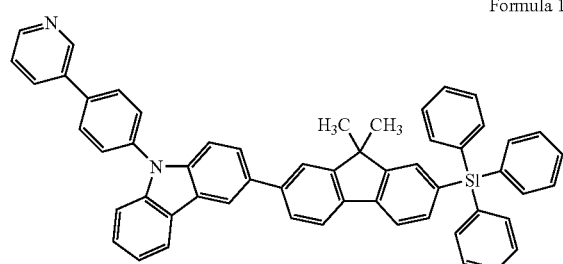
Formula 20
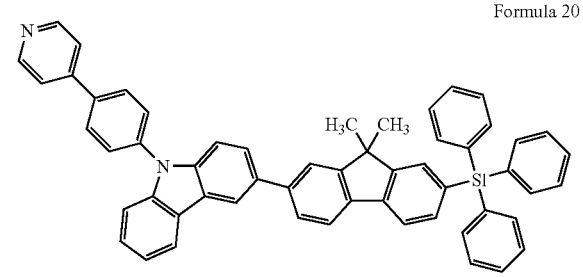
Formula 21
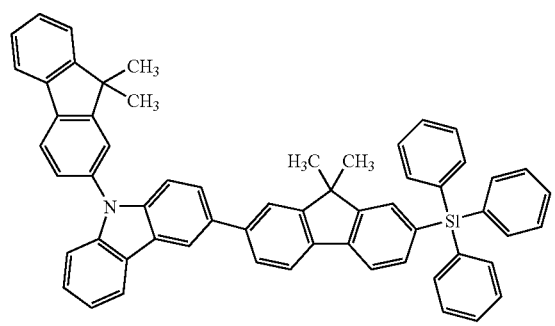
Formula 22
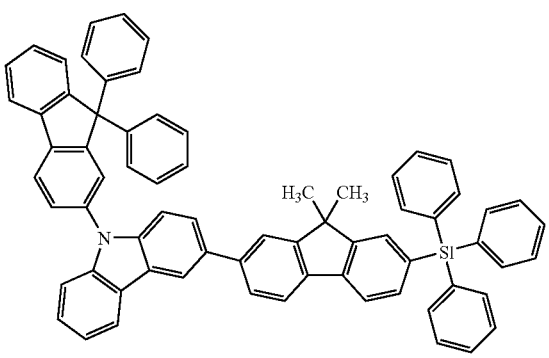

Formula 23
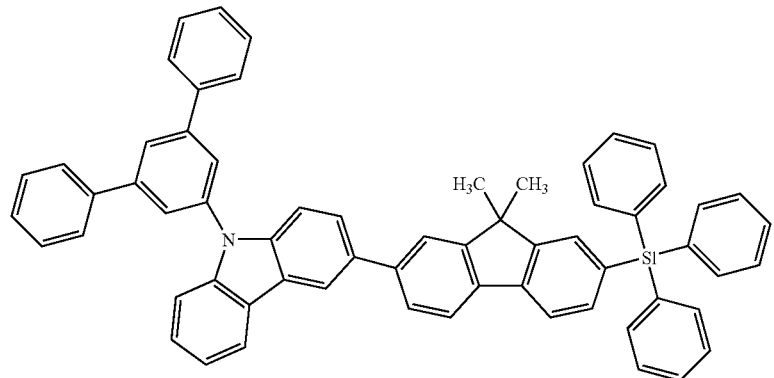
Formula 24
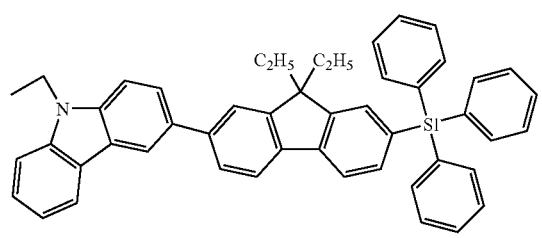
Formula 25
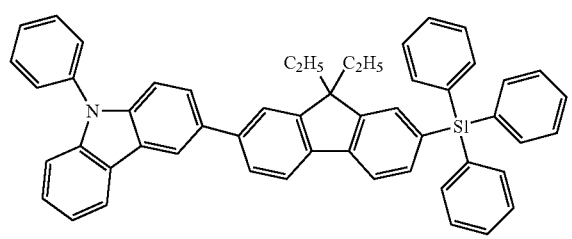
Formula 26
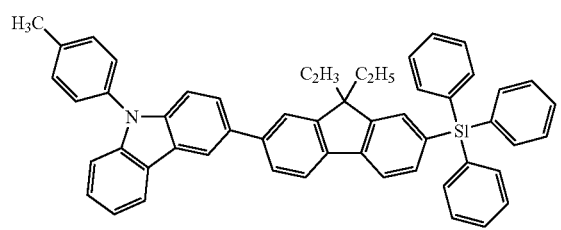
Formula 27
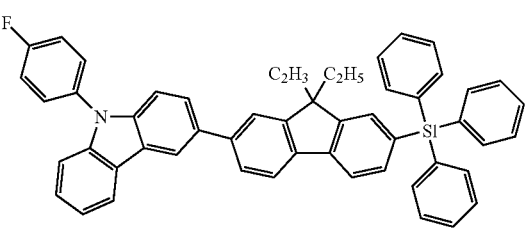
Formula 28
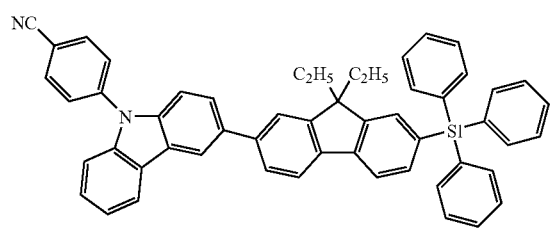
Formula 29
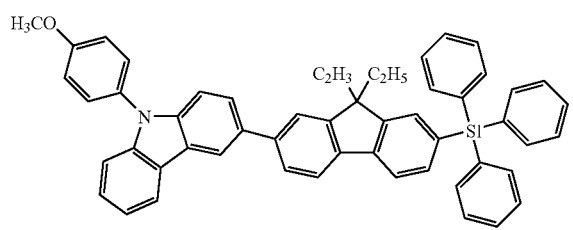
Formula 30
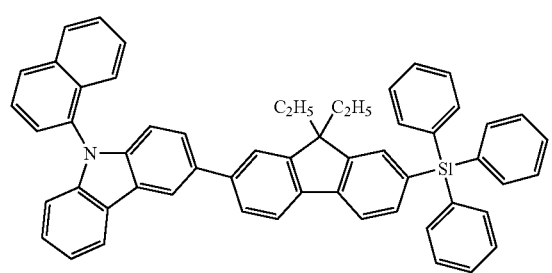
Formula 31
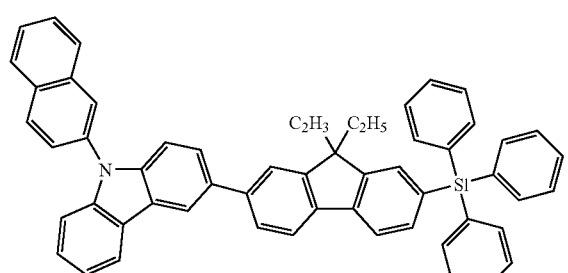

-continued
Formula 32
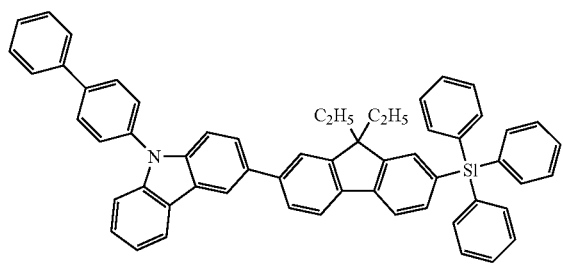
Formula 33
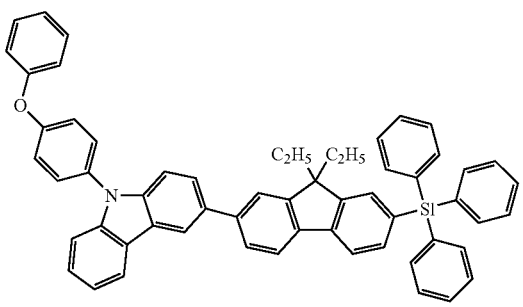
Formula 34
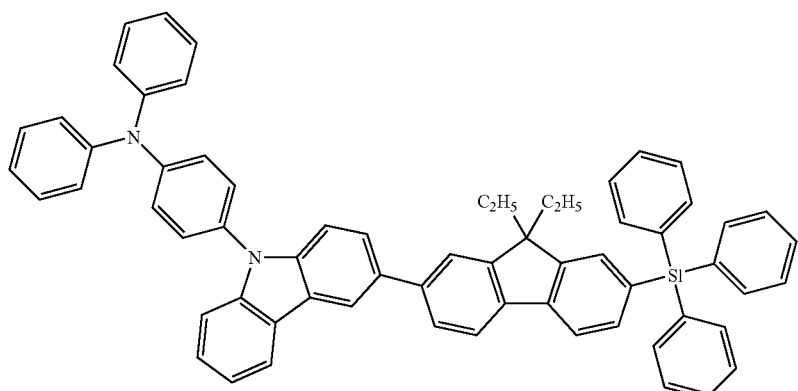
Formula 35
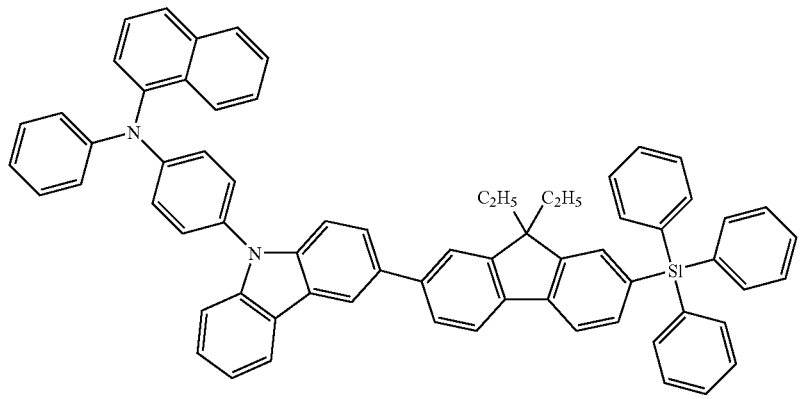
Formula 36
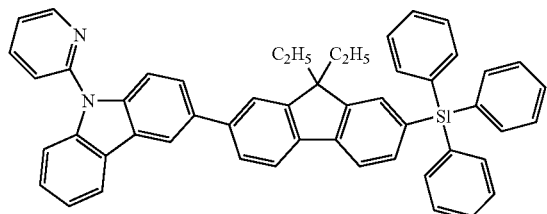
Formula 37
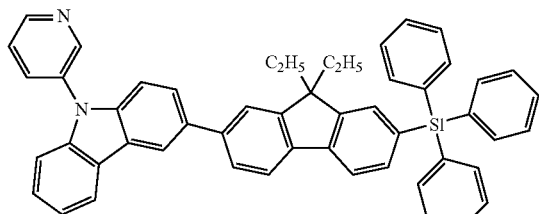
Formula 38
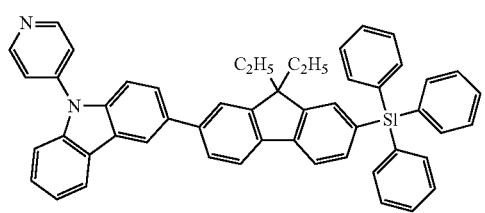
Formula 39
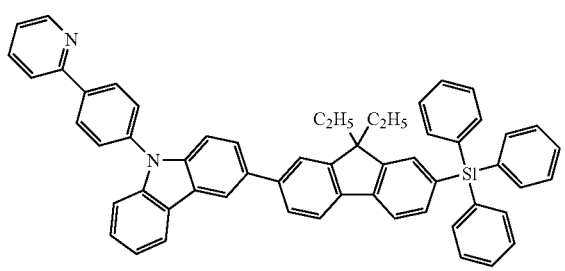

-continued
Formula 40
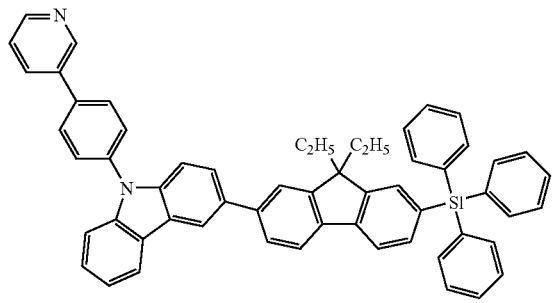
Formula 41
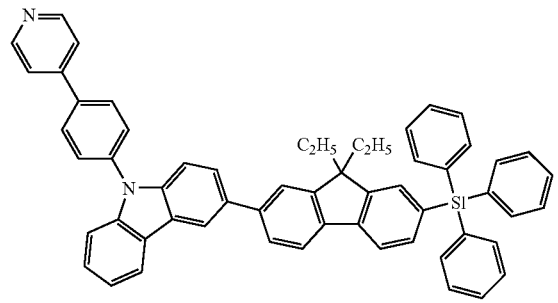
Formula 42
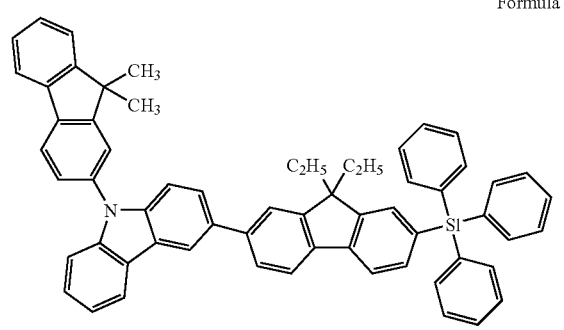
Formula 43
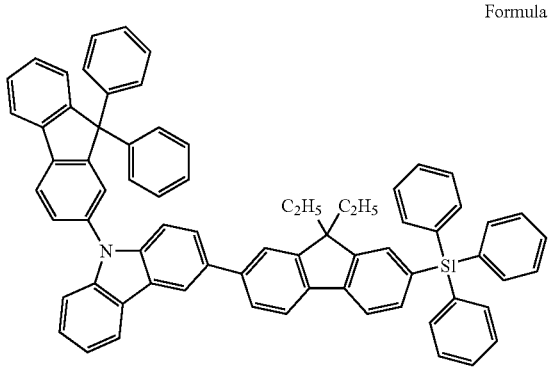
Formula 44
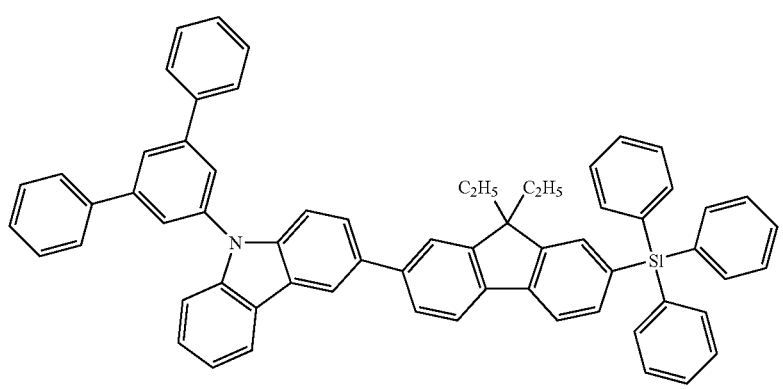
Formula 45
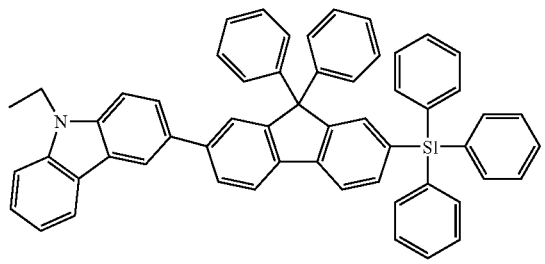
Formula 46
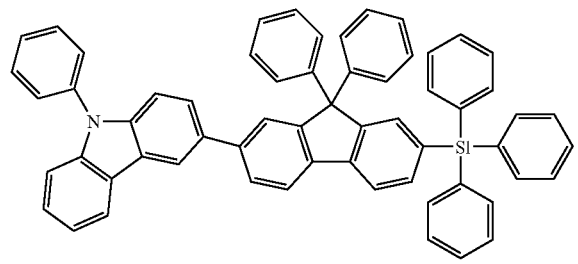
Formula 47
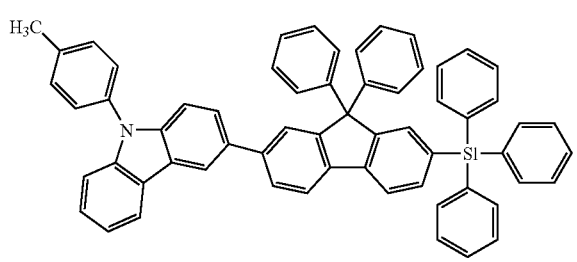
Formula 48
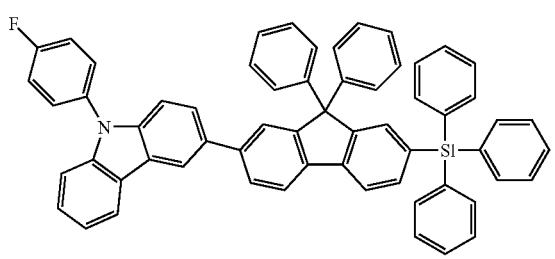

-continued
Formula 49
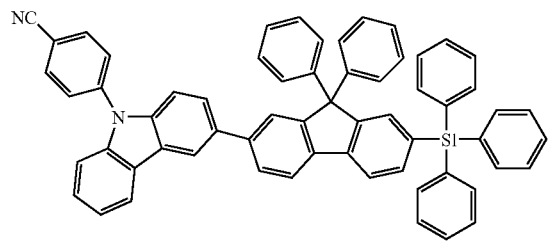
Formula 50
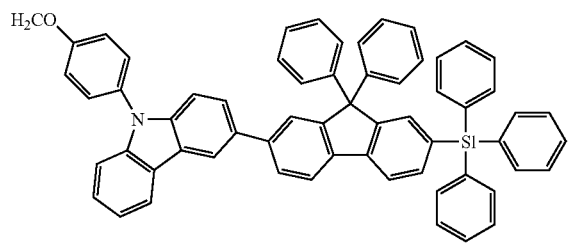
Formula 51
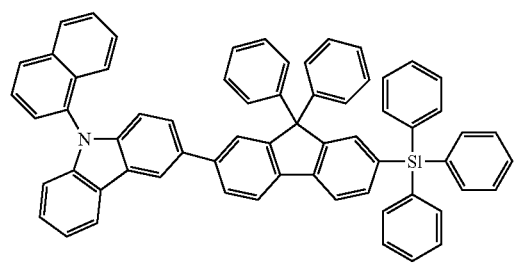
Formula 52
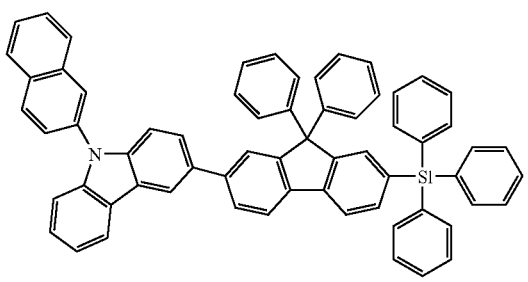
Formula 53
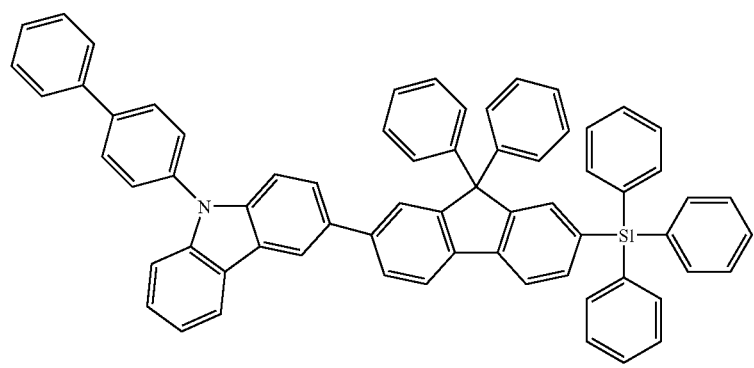
Formula 54
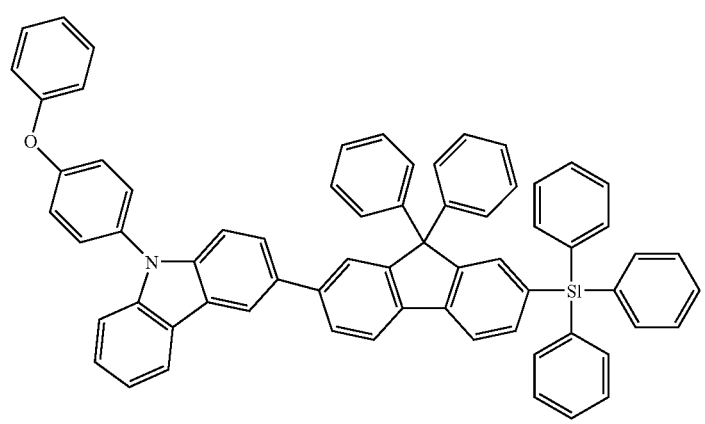

Formula 55
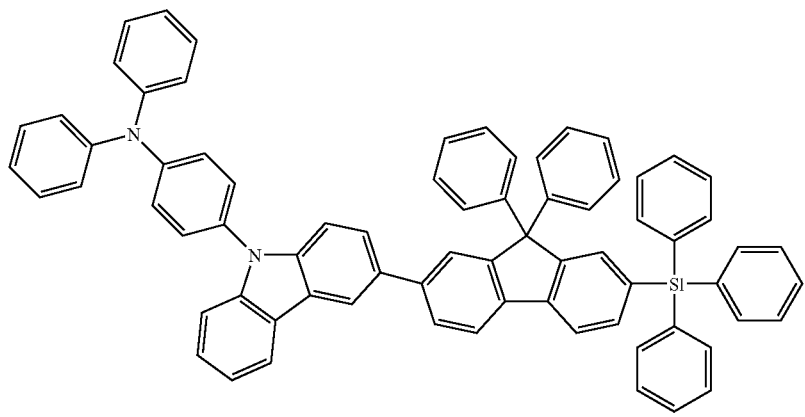
Formula 56
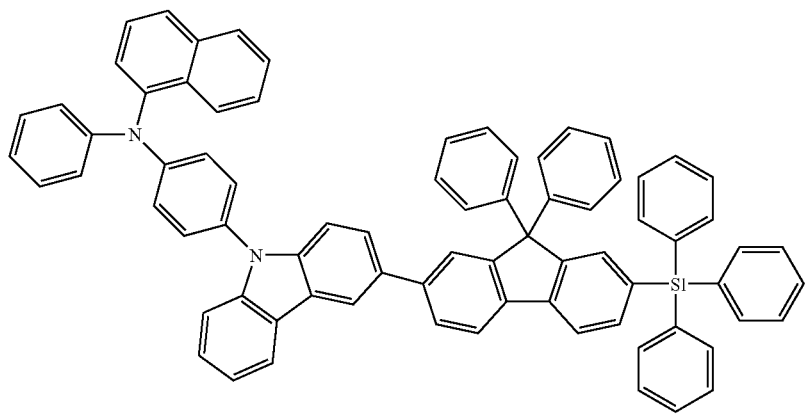
Formula 57
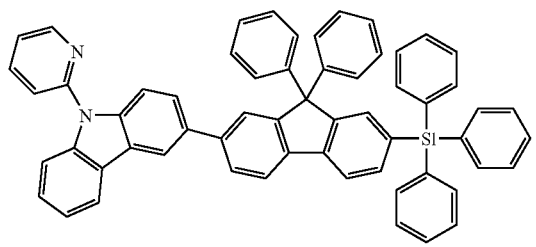
Formula 58
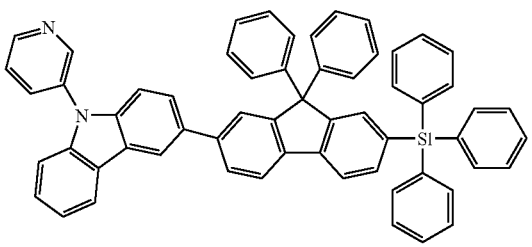
Formula 59
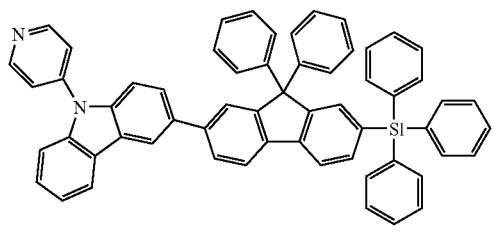
Formula 60
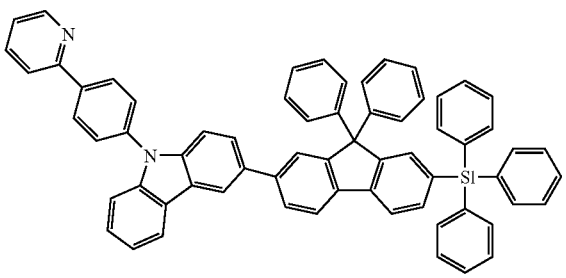

Formula 61
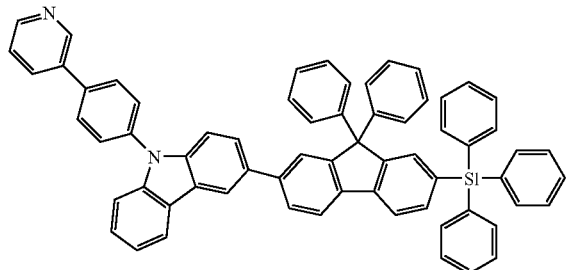

Formula 62
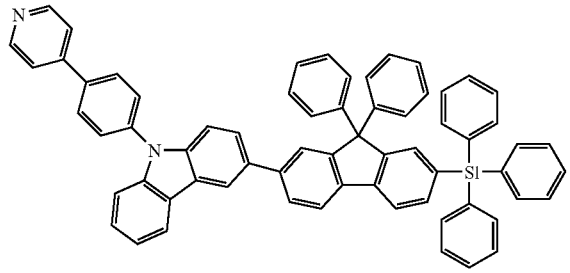

Formula 63
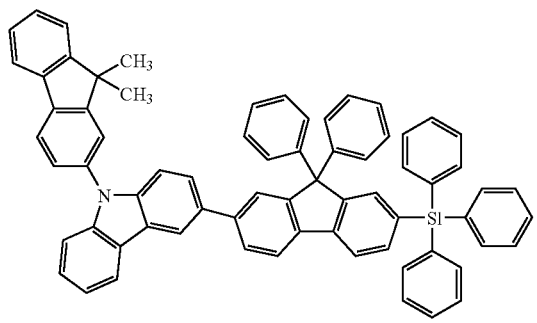

Formula 64
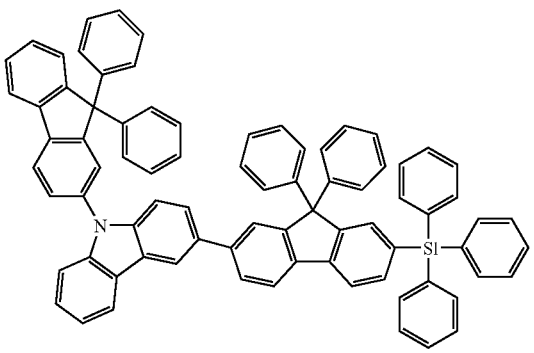

Formula 65
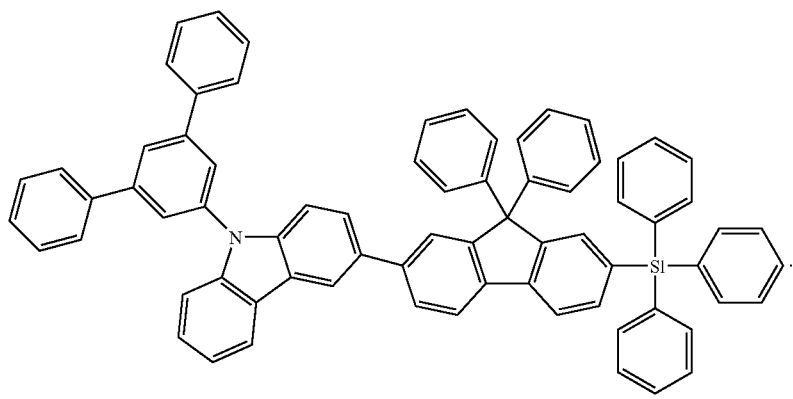

11. The organic electroluminescent device of claim 3, wherein the organic electroluminescent device is an active matrix organic electroluminescent device.

12. An organic electroluminescent device, comprising:
a first electrode;
a second electrode; and
an organic layer interposed between the first electrode and the second electrode, the organic layer comprising an emitting layer and at least one layer selected from the group consisting of a hole injection layer, a hole transport layer and a monolayer having a hole injecting capability and a hole transporting capability between the emitting layer and the first electrode, at least one of said emitting layer and said at least one layer comprising a silicon-containing compound represented by Formula 1:

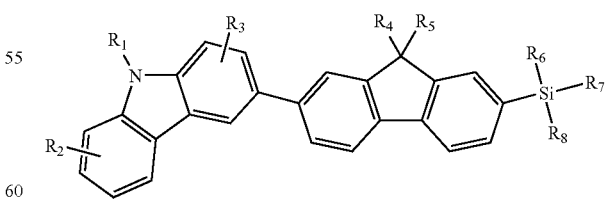
(1)

$R_1$ is selected from the group consisting of C1-C5 alkyl, phenyl, naphthyl, anthryl, biphenyl, terphenyl, fluorenyl, and pyridyl, wherein $R_1$ is unsubstituted or substituted with C1-C5 alkyl, C1-C5 alkoxy, cyano, amine, halogen, phenoxy, phenyl, or pyridyl;

R₂ and R₃ are, each independently, hydrogen, fluorine, a cyano, amino, a substituted or unsubstituted C1-C30 alkyl group, a substituted or unsubstituted C2-C30 alkenyl group, a substituted or unsubstituted C2-C20 alkynyl group, a substituted or unsubstituted C1-C30 alkoxy group, a substituted or unsubstituted C6-C30 aryloxy group, a substituted or unsubstituted C6-C20 aryl group, a substituted or unsubstituted C4-C20 heteroaryl group, or a substituted or unsubstituted C4-C20 condensed polycyclic group;

R₄ through R₇ are each independently C1-C5 alkyl or phenyl.

13. The silicon-containing compound of claim 12, wherein at least two adjacent substituents selected from the group consisting of R₄, R₅, R₆, R₇ and R₈ are connected to form a saturated or unsaturated ring.

14. The silicon-containing compound of claim 12, wherein the silicon-containing compound represented by Formula 1 is a compound represented by Formula 2:

(2)

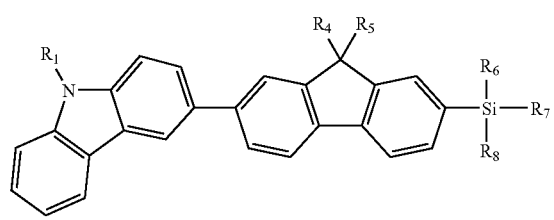

wherein R₁, R₄, R₅, R₆, R₇ and R₈ are as defined in claim 1.

15. The silicon-containing compound of claim 12, wherein R₁ is selected from the group consisting of C1-C5 alkyl, phenyl, naphthyl, anthryl, biphenyl, terphenyl, fluorenyl, and pyridyl, wherein R₁ is unsubstituted or substituted with C1-C5 alkyl, C1-C5 alkoxy, cyano, amine, halogen, phenoxy, phenyl, or pyridyl.

16. The silicon-containing compound of claim 12, wherein R₄ through R₇ are, each independently, C1-C5 alkyl or phenyl.

17. The silicon-containing compound of claim 12, wherein the silicon-containing compound is represented by one of the following structures:

(4)

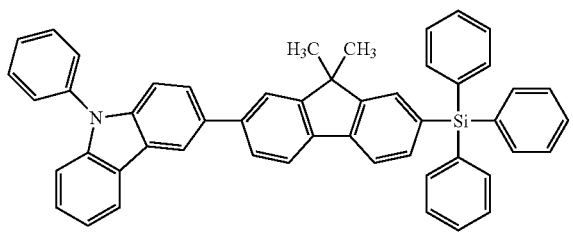

(6)

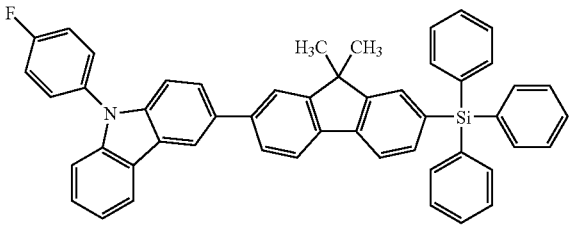

(10)

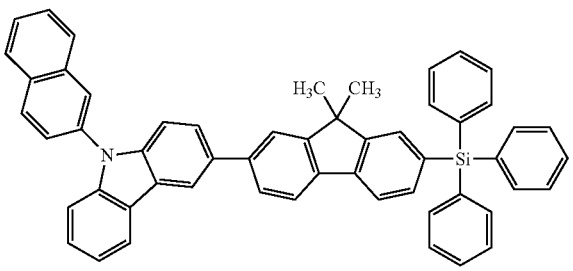

(11)

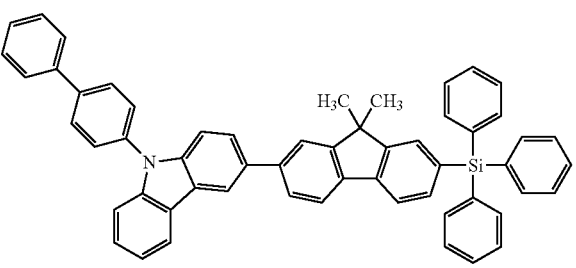

(25)

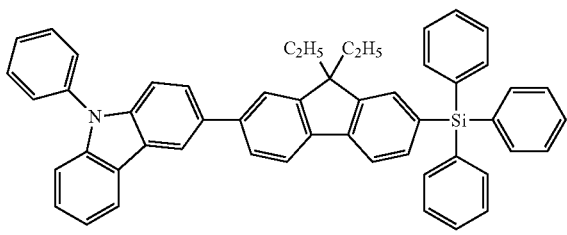

(32)

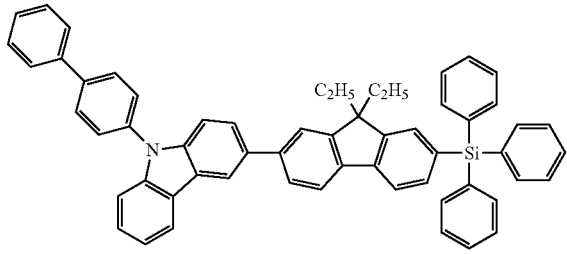

(46)
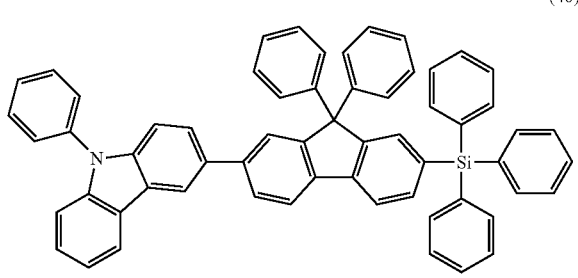
(53)
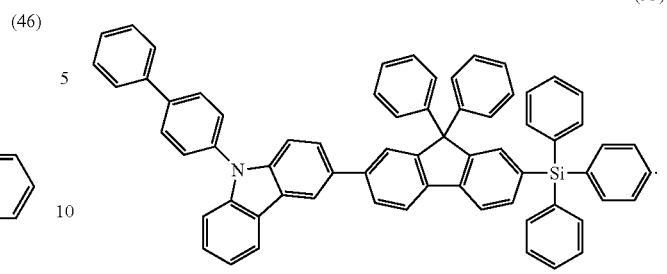
18. The silicon-containing compound of claim 12, wherein the silicon-containing compound is represented by one of the following structures:
Formula 3
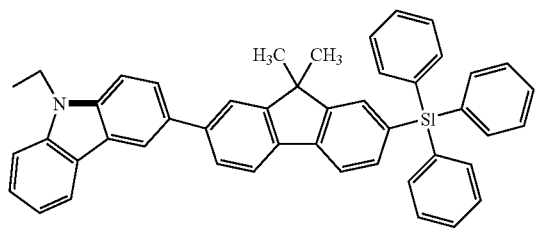
Formula 4
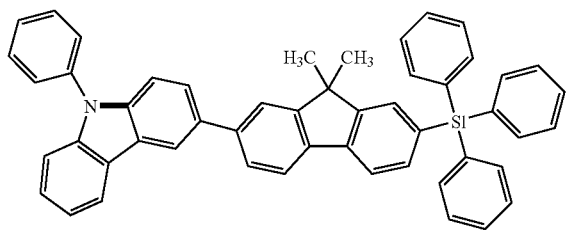
Formula 5
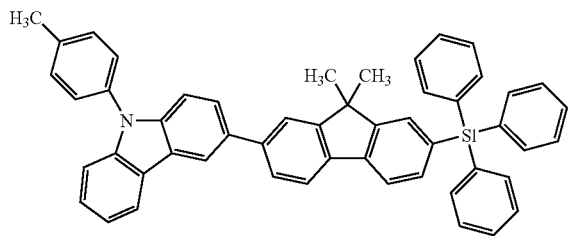
Formula 6
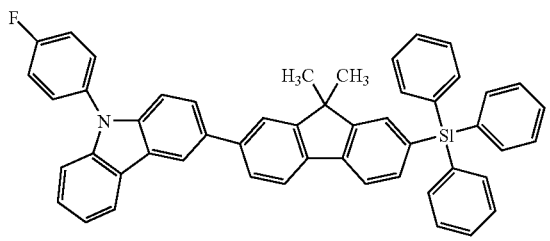
Formula 7
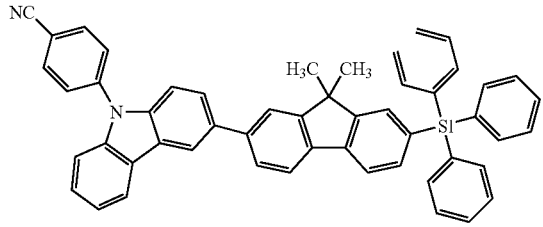
Formula 8
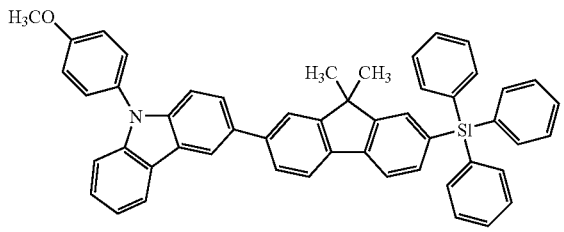
Formula 9
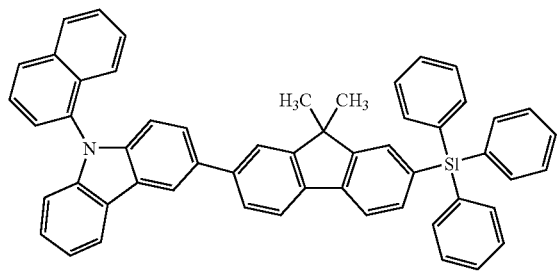
Formula 10
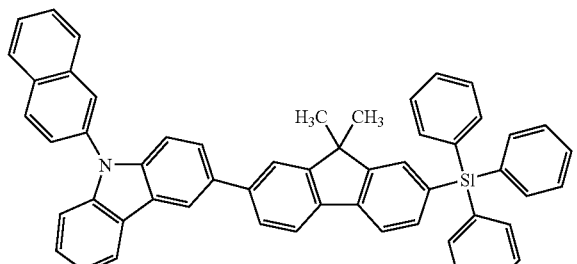

Formula 11
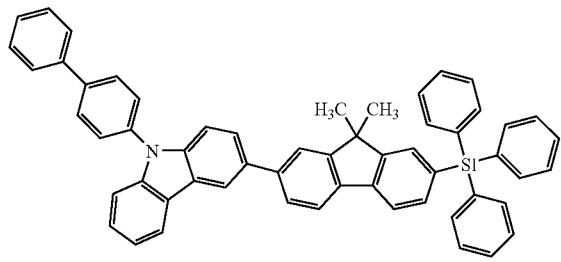
Formula 12
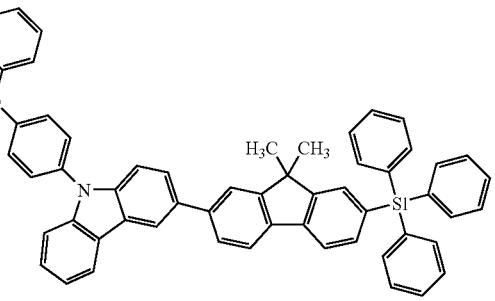
Formula 13
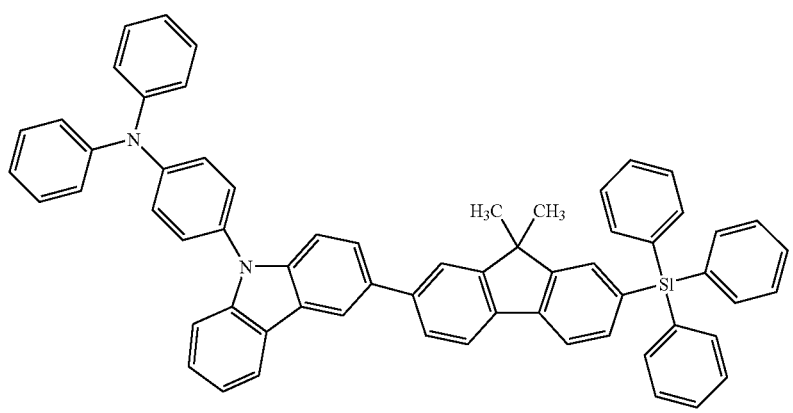
Formula 14
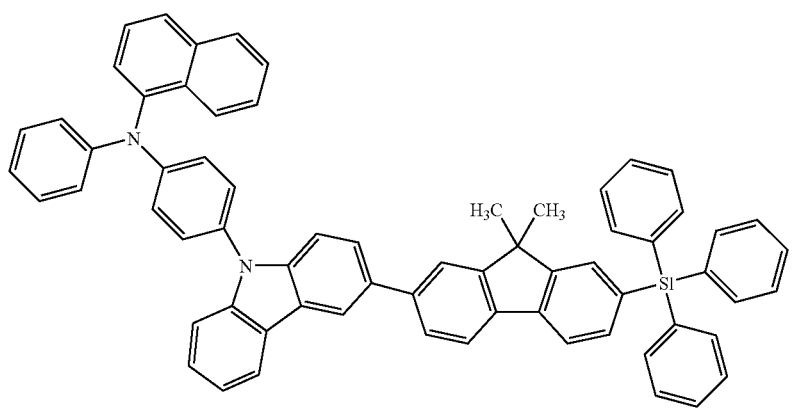
Formula 15
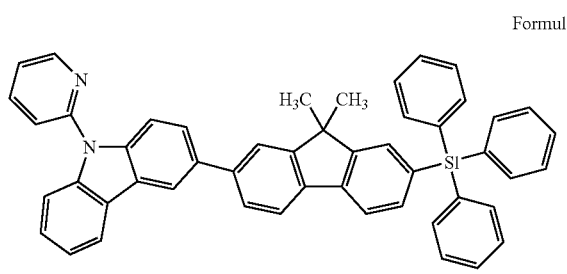
Formula 16
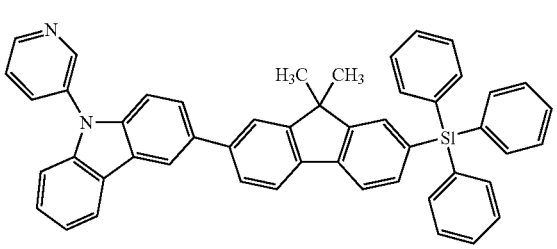

-continued
Formula 17
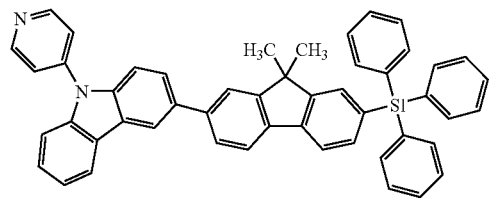
Formula 18
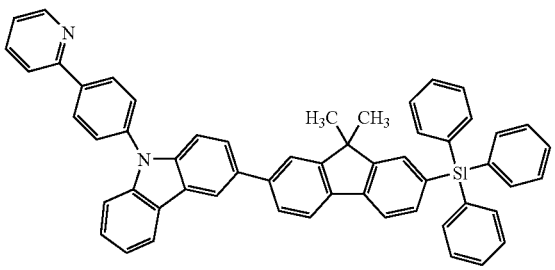
Formula 19
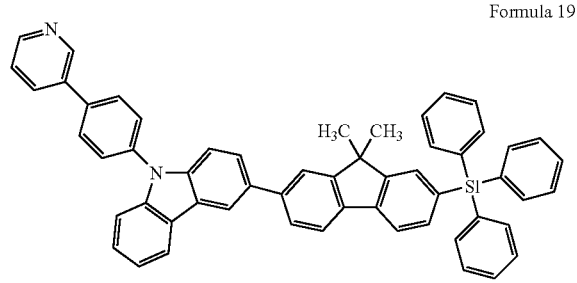
Formula 20
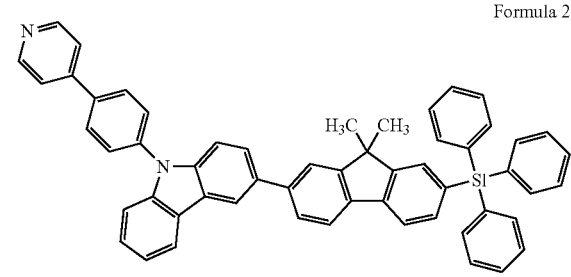
Formula 21
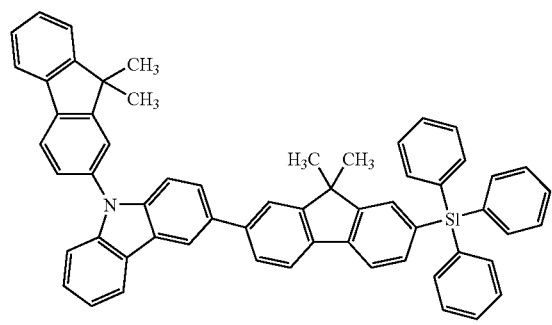
Formula 22
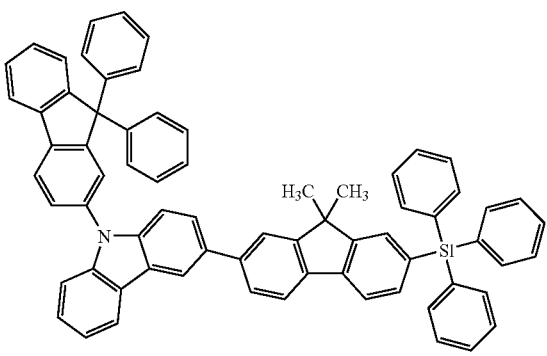
Formula 23
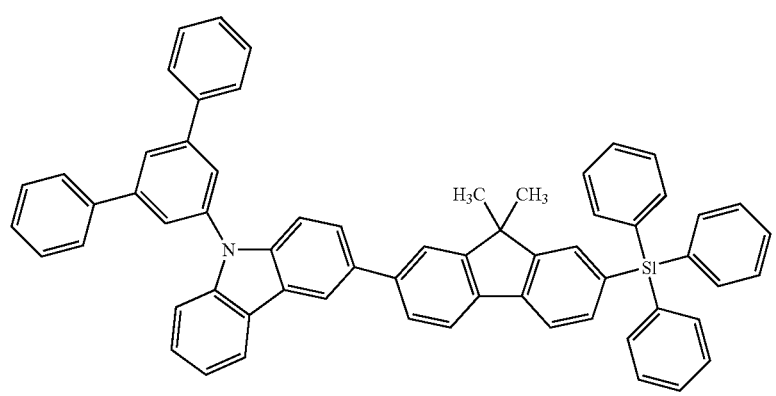
Formula 24
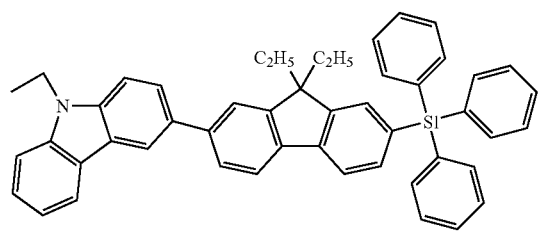
Formula 25
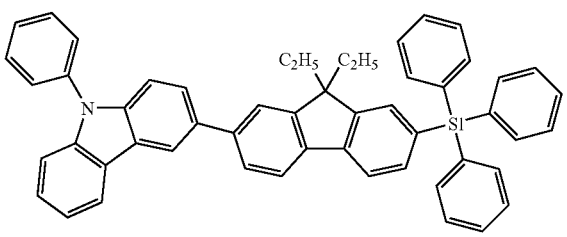

-continued
Formula 26
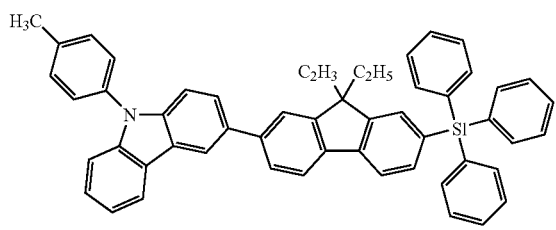
Formula 27
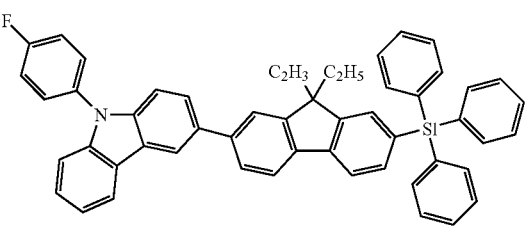
Formula 28
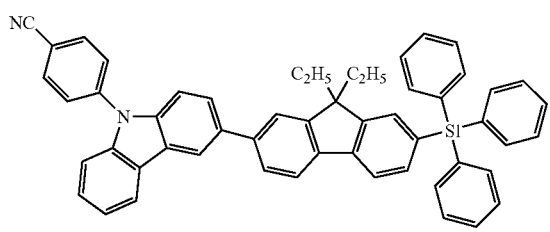
Formula 29
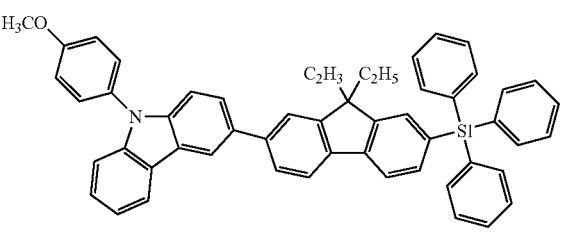
Formula 30
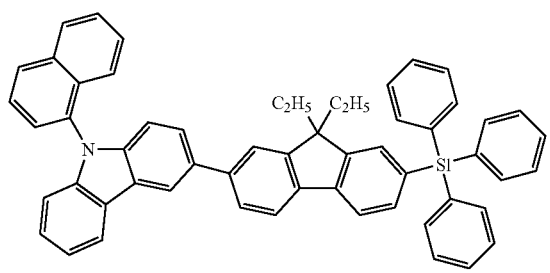
Formula 31
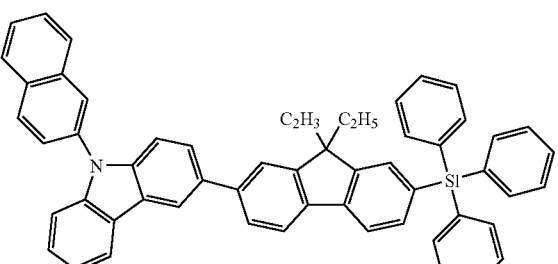
Formula 32
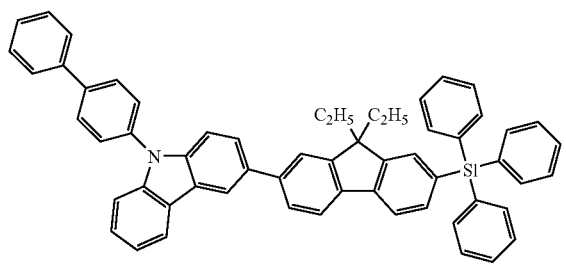
Formula 33
Formula 34
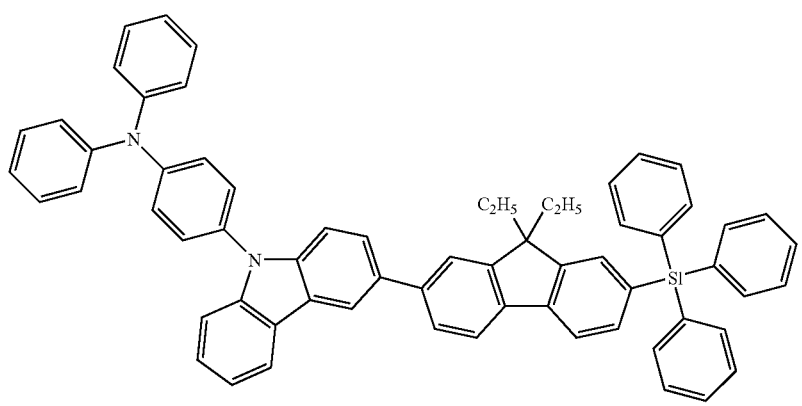

Formula 35
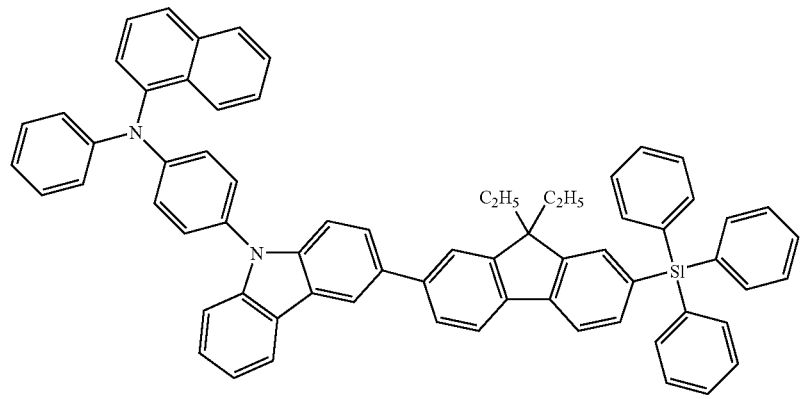
Formula 36
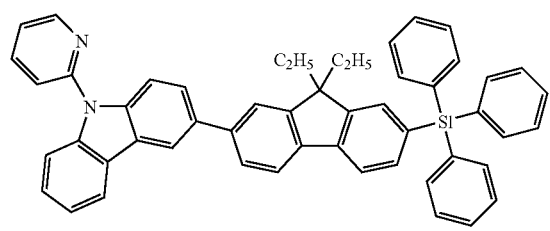
Formula 37
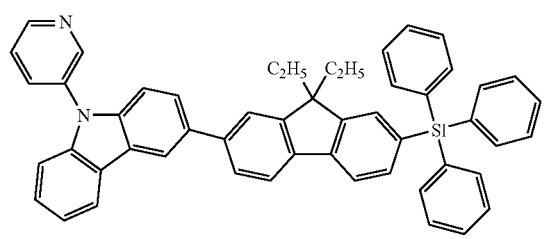
Formula 38
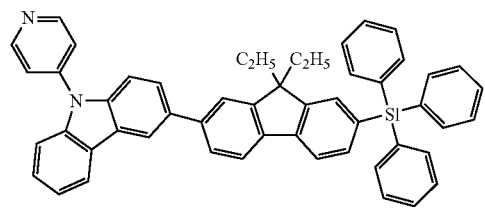
Formula 39
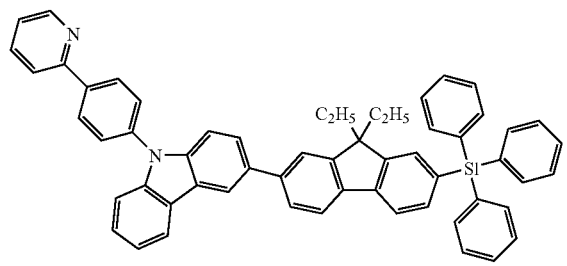
Formula 40
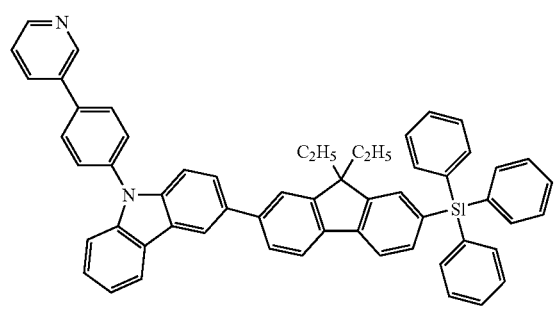
Formula 41
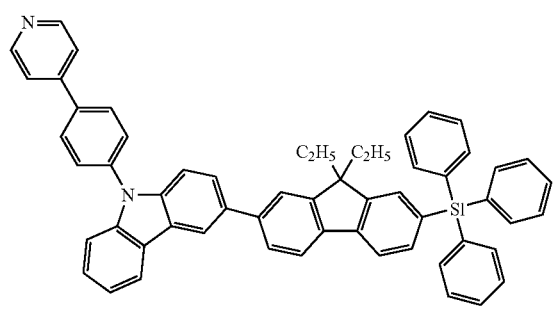
Formula 42
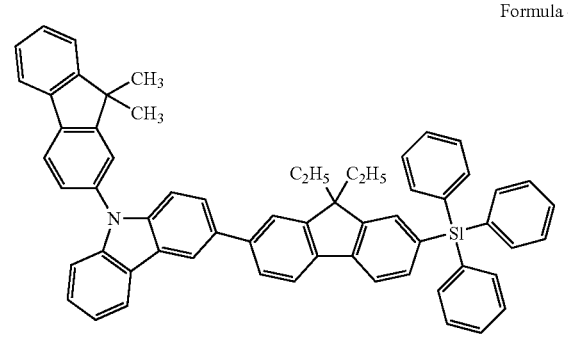
Formula 43
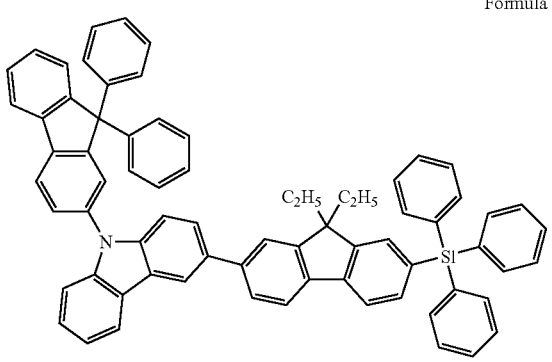

-continued
Formula 44
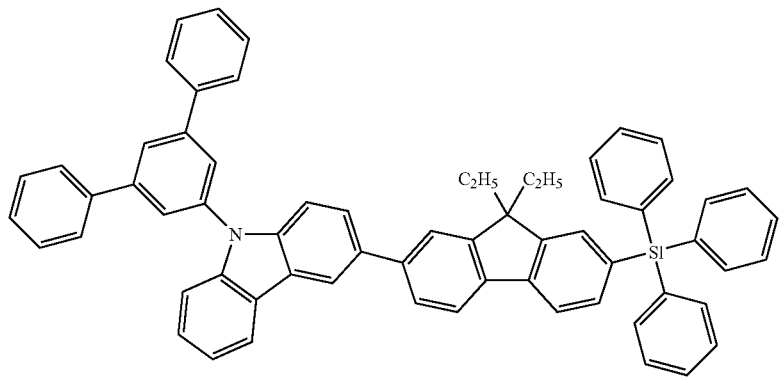
Formula 45
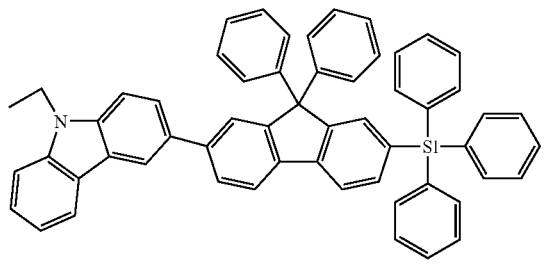
Formula 46
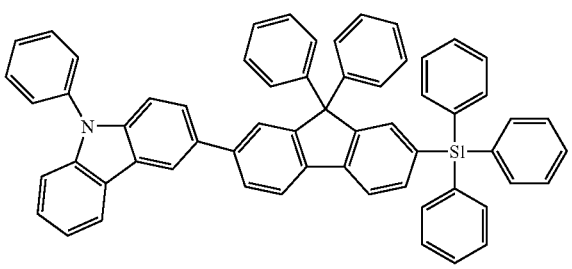
Formula 47
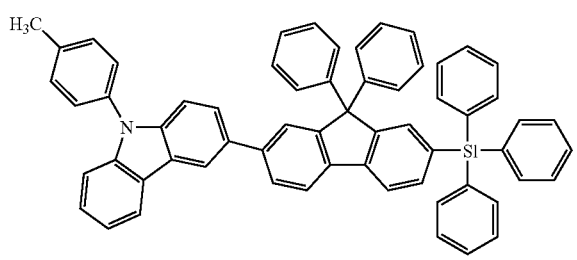
Formula 48
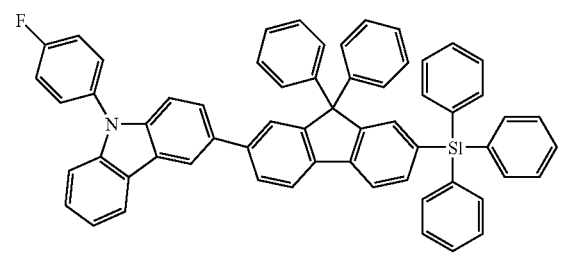
Formula 49
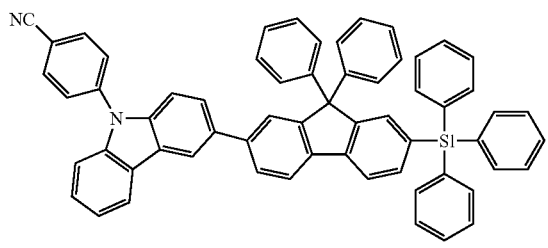
Formula 50
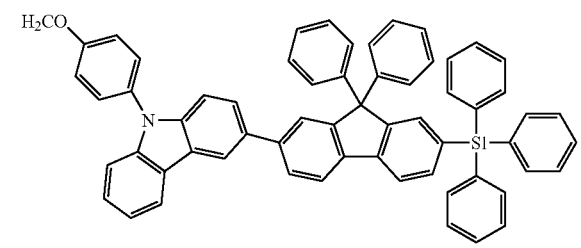
Formula 51
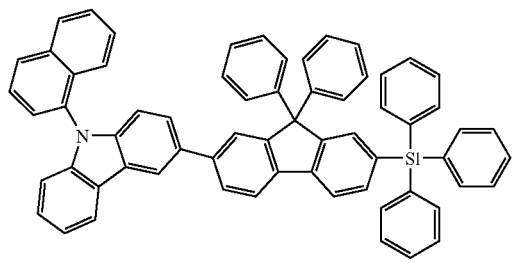
Formula 52
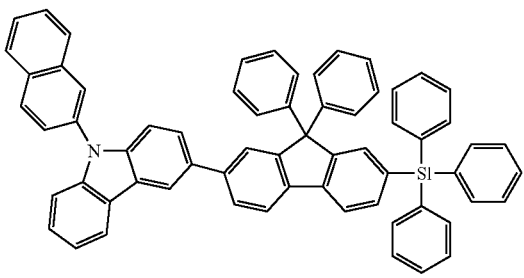

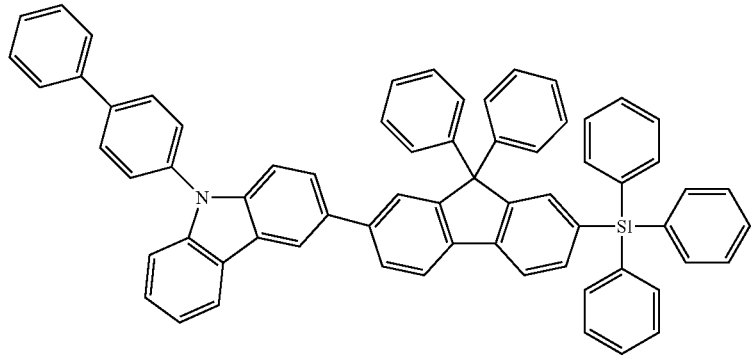
Formula 53
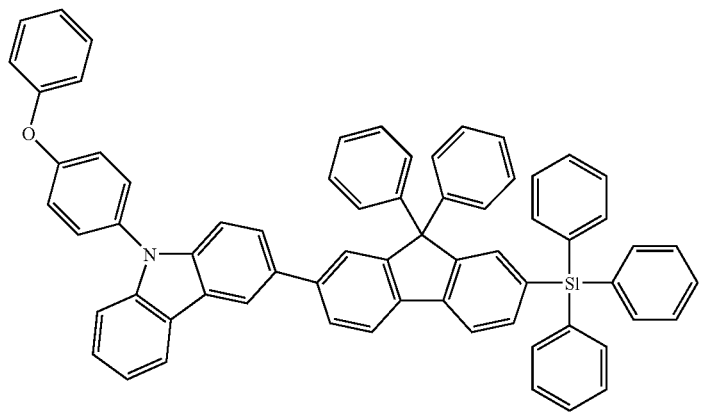
Formula 54
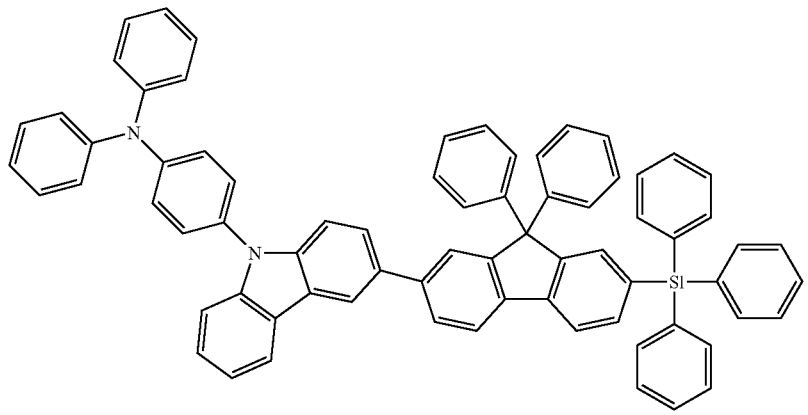
Formula 55
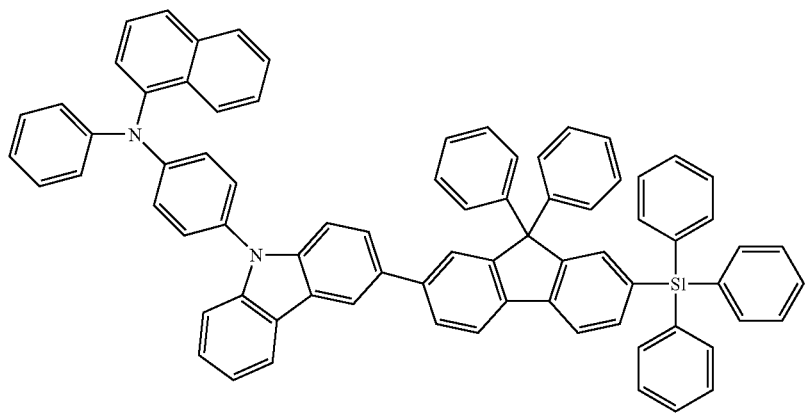
Formula 56

-continued
Formula 57
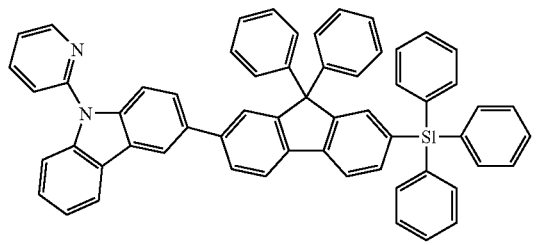
Formula 58
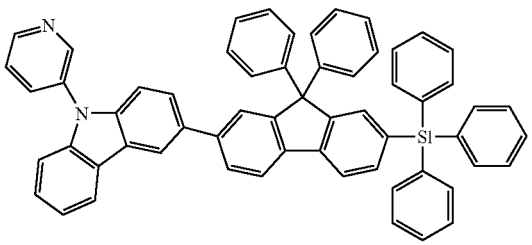
Formula 59
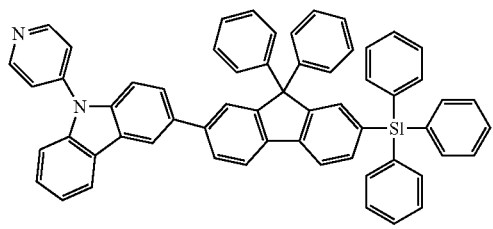
Formula 60
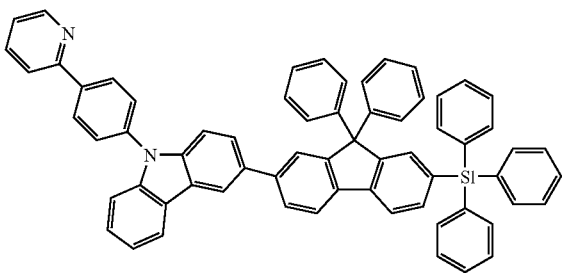
Formula 61
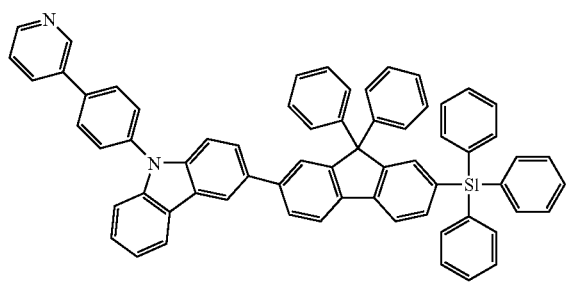
Formula 62
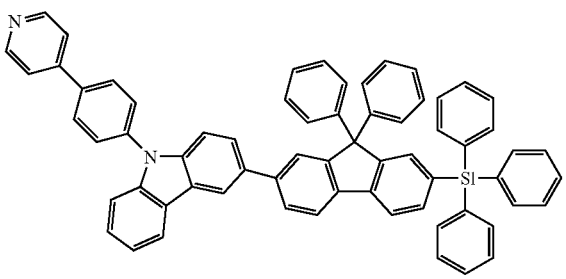
Formula 63
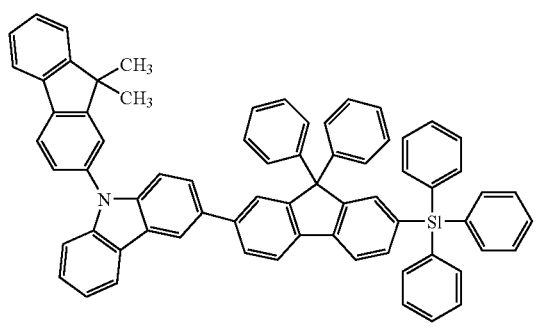
Formula 64
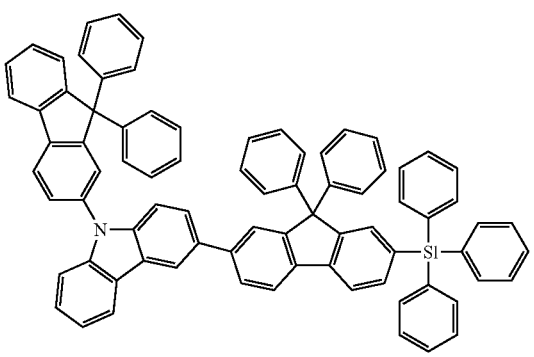
Formula 65
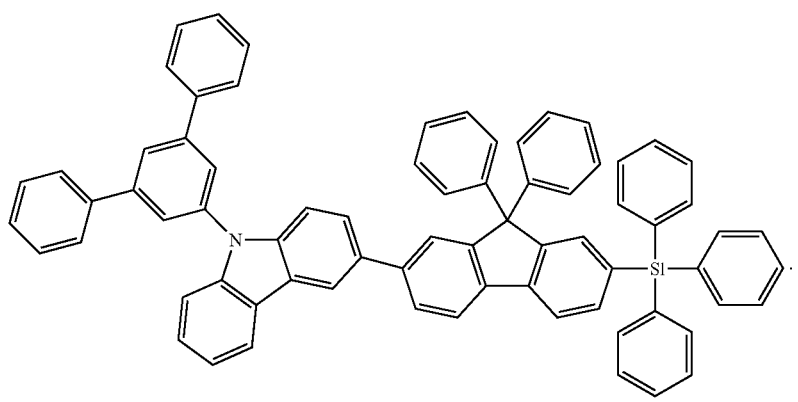

19. The organic electroluminescent device of claim 12, wherein said at least one layer comprises the hole transport layer comprising the silicon-containing compound.

20. The organic electroluminescent device of claim 12, wherein said at least one layer comprises the hole transport layer comprising the silicon-containing compound and the hole injection layer.

* * * * *